(12) United States Patent
Jones et al.

(10) Patent No.: US 6,284,456 B1
(45) Date of Patent: Sep. 4, 2001

(54) TRANSCRIPTIONAL COACTIVATOR THAT INTERACTS WITH TAT PROTEIN AND REGULATES ITS BINDING TO TAR RNA, METHODS FOR MODULATING TAT TRANSACTIVATION, AND USES THEREFOR

(75) Inventors: Katherine A. Jones, Encinitas; Ping Wei, San Diego; Mitchell Garber, Woodland Hills; Shi-Min Fang, San Diego, all of CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 09/476,482

(22) Filed: Dec. 30, 1999

Related U.S. Application Data

(63) Continuation-in-part of application No. 09/126,980, filed on Jul. 30, 1998.
(60) Provisional application No. 60/069,341, filed on Dec. 11, 1997.

(51) Int. Cl.$^7$ .............................. C12Q 1/70; A61K 38/00; C07K 1/00; C07K 16/00; C07H 21/02
(52) U.S. Cl. .............................. 435/5; 530/324; 530/350; 530/388.35; 536/23.1
(58) Field of Search .................................. 530/324, 350, 530/388.35, 23.1; 435/5

(56) References Cited

U.S. PATENT DOCUMENTS 5,278,042    1/1994    Wong-Stall et al. ...................... 435/5

OTHER PUBLICATIONS

Alonso, et al., "Human Chromosome 12 Is Required for Optimal Interactions between Tat and TAR of Human Immunodeficiency Virus Type 1 in Rodent Cells" *Journal of Virology* 66(7) 4617–4621.

Altschul, et al., "Basic Local Alignment Search Tool" *J. Mol. Biol.* 215:403–410 (1990).

Bahouth, et al., "Immunological approaches for probing receptor structure and function" *TiPS* 12:338–343 (1991).

Berger, et al., "Interaction of Glucocorticoid Analogues with the Human Glucocorticoid Receptor" 41 (3–8):733–738 (1992).

Bohjanen, et al., "A small circular TAR RNA decoy specifically inhibits Tat–activated HIV–1 transcription" *Nucleic Acids Research* 24 (19):3733–3738 (1996).

Chun and Jeang, "Requirements for RNA Polymerase II Carboxyl–terminal Domain for Activated Transcription of Human Retroviruses Human T–Cell Lymphotropic Virus I and HIV–1" *The Journal of Biological Chemistry* 271 (44):27888–27894 (1996).

Churcher, et al., "High Affinity Binding of TAR RNA by the Human Immunodeficiency Virus Type–1 tat Protein Requires Base–pairs in the RNA Stem and Amino Acid Residues Flanking the Basic Region" *J. Mol. Biol.* 230:90–110 (1993).

(List continued on next page.)

*Primary Examiner*—Hankyel T. Park
(74) *Attorney, Agent, or Firm*—Foley & Lardner; Stephen E. Reiter

(57) ABSTRACT

In accordance with the present invention, isolated nucleic acid encoding a host cell protein that regulates Tat transactivation has been discovered. The protein is the first discovered constituent of the TAK/TEFb complex which associates with the HIV Tat, via divalent cation metals, and is necessary for the binding of Tat to TAR RNA. This protein, cyclin T1, is an 87 kDa cyclin partner for the PITALRE kinase. It is further discovered that Tat must interact with TAK in order to bind to TAR RNA with affinity and with the appropriate sequence specificity that is observed in vivo. In accordance with another aspect of the invention, formulations useful for modulation of Tat transactivation have been developed. In addition, assays have been developed for the identification of compounds useful to modulate the above-described processes.

46 Claims, 3 Drawing Sheets

OTHER PUBLICATIONS

Conway and Wickens, "Analysis of mRNA 3' end formation by modification interference: the only modifications which prevent processing lie in AAUAAA and the poly(A) site" The EMBO Journal 6 (13):4177–4184 (1987).

Cullen, B. R., "Does HIV–1 TAT Induce a Change in Viral Initiation Rights?" Cell 73:417–420 (1993).

Dahmus, M. E., "Reversible Phosphorylation of the C–terminal Domain if RNA Polymerase II" The Journal of Biological Chemistry 271 (32):19009–19012 (1996).

Furnari, et al., "pch1$^+$, a Second Essential C–type Cyclin Gene in Schizosaccharomyces pombe" The Journal of Biological Chemistry 272 (18):12100–12106 (1997).

Gait and Karn, "RNA recognition by the human immunodeficiency virus Tat and Rev proteins" TIBS 18:255–259 (1993).

Garriga, et al., "The CDC2–related kinase PITALRE is the catalytic subunit of active multimeric protein complexes" Biochem J. 319:293–298 (1996).

Ghosh, et al, "Synergism between Tat and VP16 in Transactivation of HIV–1 LTR" J. Mol. Biol. 234:610–619 (1993).

Grana, et al., "PITALRE, a nuclear CDC2–related protein kinase that phosphorylates the retinoblastoma protein in vitro" Proc. Natl. Acad. Sci USA 91:3834–3838 (1994).

Guan and Dixon, "Eukaryotic Proteins Expressed in Escherichia coli: An Improved Thrombin Cleavage and Purification Procedure of Fusion Proteins with Glutathione S–Transferase" Analytical Biochemistry 192:262–267 (1991).

Hamy, et al., "An inhibitor of the Tat/TAR RNA interaction that effectively suppresses HIV–1 replication" Proc. Natl. Acad. Sci. USA 94:3548–3553 (1997).

Hart, et al., "A Human Chromosome 12–Associated 83–Kilodalton Cellular Protein Specifically Binds to the Loop Region of Human Immunodeficiency Virus Type 1 trans–Activation Response Element RNA" Journal of Virology 69 (10):6593–6599 (1995).

Hart, et al., "Human Chromosome 12 Is Required for Elevated HIV–1 Expression in Human–Hamster Hybrid Cells" Science 246:488–491 (1989).

Hart, et al., "TAR Loop–Dependent Human Immunodeficiency Virus trans Activation Requires Factors Encoded on Human Chromosome 12" Journal of Virology 67 (8):5020–5024 (1993).

Herrmann, et al., "Specific Interaction of the Human Immunodeficiency Virus Tat Proteins with a Cellular Protein Kinase" Virology 197:601–608 (1993).

Herrmann, et al., "Lentivirus Tat Proteins Specifically Associate with a Cellular Protein Kinase, TAK, That Hyperphosphorylates the Carboxyl–Terminal Domain of the Large Subunit of RNA Polymerase II: Candidate for a Tat Cofactor" Journal of Virology 69 (3):1612–1620 (1995).

Hollenberg, et al., "Multiple and Cooperative Trans–Activation Domains of the Human Glucocorticoid Receptor" Cell 55:899–906 (1988).

Huang, et al., "Anti–HIV Agents That Selectively Target Retroviral Nucleocapsid Protein Zinc Fingers without Affecting Cellular Zinc Finger Proteins" J. Med. Chem. 41:1371–1381 (1998).

Jones and Peterlin, "Control of RNA Initiation and Elongation at the HIV–1 Promoter" Annu. Rev. Biochem. 63:717–743 (1994).

Jones, K. A., "Taking a new TAK on Tat transactivation" Genes & Development 11:2593–2599 (1997).

Kao, et al., "Anti–termination of transcription within the long terminal repeat of HIV–1 by tat gene product" Nature 330:489–493 (1987).

Kozak, M., "Structural Features in Eukaryotic mRNAs That Modulate the Initiation of Translation" The Journal of Biological Chemistry 266 (30):19867–19870 (1991).

Laspia, et al., "HIV–1 Tat Overcomes Inefficient Transcriptional Elongation in Vitro" J. Mol. Biol. 232:732–746 (1993).

Lee and Greenleaf, "Modulation of RNA Polymerase II Elongation Efficiency by C–terminal Heptapeptide Repeat Domain Kinase I" The Journal of Biological Chemistry 272 (17):10990–10993 (1997).

Luo and Peterlin, "Juxtaposition between Activation and Basic Domains of Human Immunodeficiency Virus Type 1 Tat Is Required for Optimal Interactions between Tat and TAR" Journal of Virology 67 (6):3441–3445 (1993).

Luo, et al., "Functional Analysis of Interactions between Tat and the trans–Activation Response Element of Human Immunnodeficiency Virus Type I in Cells" Journal of Viriology 67 (9):5617–5622 (1993).

Madore and Cullen, "Genetic Analysis of the Cofactor Requirement for Human Immunodeficiency Virus Type 1 Tat Function" Journal of Virology 67 (7):3703–3711 (1993).

Maldonado and Reinberg, "News on initiation and elongation of transcription by RNA polymerase II" Current Opinion in Cell Biology 7:352–361 (1995).

Mancebo, et al., "P–TEFb kinase is required for HIV Tat transcription activation in vivo and in vitro" Genes & Development 11:2633–2644 (1997).

Mangelsdorf, et al., "A Direct Repeat in the Cellular Retinol–Binding Protein Type II Gene Confers Differential Regulation by RXR and RAR" Cell__:555–561 (1991).

Mangelsdorf, et al., "Nuclear receptor that identifies a novel retinoic acid response pathway" Nature 345 (6272):224–229 (1990).

Marciniak and Sharp, "HIV–1 Tat protein promotes formation of more–processive elongation complexes" The EMBO Journal 10 (13):4189–4196 (1991).

Marciniak, et al., "HIV–1 Tat Protein Trans–Activates Transcription in Vitro" Cell 63:791–802 (1990).

Marshall and Price, "Purification of P–TEFb, a Transcription Factor Required for the Transition into Productive Elongation" The Journal of Biological Chemistry 270 (21):12335–12338 (1995).

Marshall, et al., "Control of RNA Polymerase II Elongation Potential by a Novel Carboxyl–terminal Domain Kinase" The Journal of Biological Chemistry 271 (43):27176–27183 (1996).

McDonnell, et al., "Zinc Ejection as a New Rationale for the Use of Cystamine and Related Disulfide–Containing Antiviral Agents in the Treatment of AIDS" J. Med. Chem. 40:1969–1976 (1997).

Needleman and Wunsch, "A General Method Applicable to the Search for Similarities in the Amino Acid Sequence of Two Proteins" J. Mol. Biol. 48:443–453 (1970).

Newstein, et al., "A Chimeric Human Immunodeficiency Virus Type I TAR Region Which Mediates High Level Trans–activation in Both Rodent and Human Cells" Virology 197:825–828 (1993).

Newstein, et al., "Human Chromosome 12 Encodes a Species–Specific Factor Which Inceases Human Immunodeficiency Virus Type II tat–Mediated trans Activation in Rodent Cells" *Journal of Virology* 64 (9):4565–4567 (1990).

Okamoto, et al., "Trans–activation by human immunodeficiency virus Tat protein requires the C–terminal domain of RNA polymerase II" *Proc. Natl. Acad. Sci. USA* 93:11575–11579 (1996).

Parada and Roeder, "Enhanced processivity of RNA polymerase II triggered by Tat–induced phosphorylation of its carboxy–terminal domain" *Nature* 384:375–384 (1996).

Pearson and Lipman, "Improved tools for biological sequence comparison" *Proc. Natl. Acad. Sci. USA* 85:2444–2448 (1988).

Rechsteiner and Rogers, "PEST sequences and regulation by proteolysis" *TIBS* 21:267–271 (1996).

Rhim and Rice, "Functional Significance of the Dinucleotide Bulge in Stem–Loop1 and Stem–Loop2 of HIV–2 TAR RNA" *Virology* 202:202–211 (1994).

Rhim, et al., "Wild–Type and Mutant HIV–1 and HIV–2 Tat Proteins Expressed in *Escherichia coli* as Fusions with Glutathione S–Transferase" *Journal of Acquired Immune Deficiency Syndromes* 7(11):1116–1121 (1994).

Rice and Carlotti, "Mutational Analysis of the Conserved Cysteine–Rich Region of the Human Immunodeficiency Virus Type I Tat Protein" *Journal of Virology* 64 (4):1864–1868 (1990).

Rice, et al., "Azodicarbonamide inhibits HIV–1 replication by targeting the nucleocapsid protein" *Nature* 3(3):341–345 (1997).

Rice, et al., "Evaluation of Selected Chemotypes in Coupled Cellular and Molecular Target–Based Screens Identifies Novel HIV–1 Zinc Finger Inhibitors" *J. Med. Chem.* 39:3606–3616 (1996).

Rice, et al., "Inhibition of HIV–1 infectivity by zinc–ejecting aromatic C–nitroso compounds" *Nature* 361:473–475 (1993).

Rice, et al., "Inhibitors of HIV Nucleocapsid Protein Zinc Fingers as Candidates for the Treatment of Aids" *Science* 270:1194–1197 (1995).

Serizawa, et al., "Phosphorylation of C–terminal domain of RNA polymerase II is not required in basal transcription" *Nature* 363:371–374 (1993).

Sheline, et al., "Two distinct nuclear transcription factors recognize loop and bulge residues of the HIV–1 TAR RNA hairpin" *Genes & Development* 5:2508–2520 (1991).

Sheridan, et al., "Acitivation of the HIV–1 enhancer by the LEF–1 HMG protein on nucleosome–assembled DNA in vitro" *Genes & Development* 9:2090–2104 (1995).

Shilatifard, et al., "Mechanism and regulation of transcriptional elongation and termination by RNA polymerase" *Current Opinion in Genetics & Development* 7:199–204 (1997).

Sterner, et al., "The Yeast Carboxyl–Terminal Repeat Domain Kinase CTDK–I Is a Divergent Cyclin–Cyclin–Dependent Kinase Complex" *Molecular and Cellular Biology* 15 (10):5716–5724 (1995).

Sullenger, et al., "Analysis of trans–Acting Response Decoy RNA–Mediated Inhibition of Human Immunodeficiency Virus Type I Transactivation" *Journal of Virology* 65 (12):6811–6816 (1991).

Sullenger, et al., "Overexpression of TAR Sequences Renders Cells Resistant to Human Immunodeficiency Virus Replication" *Cell* 63:601–608 (1990).

Sutton, et al., "Requirement for HIV–1 TAR Sequences for Tat Activation in Rodent Cells" *Virology* 206:690–694 (1995).

Tiley, et al., "The VP16 transcription activation domain is functional when targeted to a promoter–proximal RNA sequence" *Genes & Development* 6:2077–2087 (1992).

Waterman, et al., "A thymus–specific member of the HMG protein family regulates the human T cell receptor C$\alpha$ enhancer" *Genes & Development* 5:656–669 (1991).

Webster, et al., "The Hormone–Binding Domains of the Estrogen and Glucocorticoid Receptors Contain an Inducible Transcription Activation Function" *Cell* 54:199–207 (1988).

Webster, et al., "The Yeast $UAS_G$ Is a Transcriptional Enhancer in Human HeLa Cells in the Presence of the GAL4 Trans–Activator" *Cell* 52:169–178 (1988).

Yang, et al., "TAK, an HIV Tat–associated kinase, is a member of the cyclin–dependent family of protein kinases and is induced by activation of peripheral blood lymphocytes and differentiation of promonocytic cell lines" *Proc. Natl. Acad. Sci. USA* 94:12331–12336 (1997).

Yang, et al., "The Human Immunodeficiency Virus Tat Protein Specifically Associated with TAK In Vivo and Require the Carboxyl–Terminal Domain of RNA Polymerase II for Function" *Journal of Virology* 70 (7):4576–4584 (1986).

Zhu, et al., "Transcription elongation factor–P–TEFb is required for HIV–1 Tat transactivation in vitro" *Genes & Development* 11:2622–2632 (1997).

| | | |
|---|---|---|
| (SEQ ID NO:2) | hCyc-K  11 | RWYFTREQLENSPSRRFGVDPDKELSYRQQAANLLQDMGQRLN - VSQLTINTAIVYMHRFYMIQ |
| (SEQ ID NO:6) | ceYL34  19 | KWLFTKEEMKKTASIQEGMSREELASRQMAAAFIQEMIDGLN(8)IGHTGLCVAHTMHRFYYLH |
| (SEQ ID NO:7) | spCyc-C 17 | QWIISKDQLVFTPSALDGIPLDQEEIQRSKGCNFIINVGLRLK - LPQTALATANIYFHRFYLRF |
| (SEQ ID NO:8) | hCyc-C  30 | YLQWILDKQDLLKERQKDLKFLSEEEYWKLQIFFTNVIQALGE(4)LRQQVIATATVYFKRFYARY |
| (SEQ ID NO:9) | hCyc-H  31 | FRCKAVANGKVLPNDPVFLEPHEEMTLCKYYEKRLLEFCSVFKPAMPRSVVGTACMYFKRFYYLNN |

■ H1    ■ H2

| | | |
|---|---|---|
| hCyc-K  | 74 | SFTQFPGNSVAPAALFLAAKVEEQPKKLEHVIKVAHTCLHPQESLPDTRSEAYLQQVQDLVILESI |
| ceYL34  | 90 | SFKKYDYRDVGAACVFLAGKSQECFRKLSHVISWRERKDRKQLNNTTETARNEAAQIIVLLESM |
| spCyc-C | 80 | SLKNYHYYEVAATCIFLATKVEDSVRKLRDIVINCAKVAQKNSNVLVDEQTKEYWRDXVILYTE |
| hCyc-C  | 97 | SLKSIDPVLMAPTCVFLASKVEEFGVVSNTRLIAAATSVLKTRFSYAFPKEFPYRMNHILECEFYL |
| hCyc-H  | 95 | SVMEYHPRIIMLTCAFLACKVDEFNVSSPQFVGNLRESPLGQEKALEQILEYELLIQQLNFHLIV |

SEQUENCE LISTING

<160> NUMBER OF SEQ ID NOS: 19

<210> SEQ ID NO 1
<211> LENGTH: 2181
<212> TYPE: DNA
<213> ORGANISM: Homo sapiens
<220> FEATURE:
<221> NAME/KEY: CDS
<222> LOCATION: (1)...(2178)

<400> SEQUENCE: 1

```
atg gag gga gag agg aag aac aac aac aaa cgg tgg tat ttc act cga      48
Met Glu Gly Glu Arg Lys Asn Asn Asn Lys Arg Trp Tyr Phe Thr Arg
 1               5                  10                  15 gaa cag ctg gaa aat agc cca tcc cgt cgt ttt ggc gtg gac cca gat      96
Glu Gln Leu Glu Asn Ser Pro Ser Arg Arg Phe Gly Val Asp Pro Asp
                20                  25                  30 aaa gaa ctt tct tat cgc cag cag gcg gcc aat ctg ctt cag gac atg     144
Lys Glu Leu Ser Tyr Arg Gln Gln Ala Ala Asn Leu Leu Gln Asp Met
            35                  40                  45 ggg cag cgt ctt aac gtc tca caa ttg act atc aac act gct ata gta     192
Gly Gln Arg Leu Asn Val Ser Gln Leu Thr Ile Asn Thr Ala Ile Val
        50                  55                  60 tac atg cat cga ttc tac atg att cag tcc ttc aca cag ttc cct gga     240
Tyr Met His Arg Phe Tyr Met Ile Gln Ser Phe Thr Gln Phe Pro Gly
    65                  70                  75                  80 aat tct gtg gct cca gca gcc ttg ttt cta gca gct aaa gtg gag gag     288
Asn Ser Val Ala Pro Ala Ala Leu Phe Leu Ala Ala Lys Val Glu Glu
                85                  90                  95 cag ccc aaa aaa ttg gaa cat gtc atc aag gta gca cat act tgt ctc     336
Gln Pro Lys Lys Leu Glu His Val Ile Lys Val Ala His Thr Cys Leu
               100                 105                 110 cat cct cag gaa tcc ctt cct gat act aga agt gag gct tat ttg caa     384
His Pro Gln Glu Ser Leu Pro Asp Thr Arg Ser Glu Ala Tyr Leu Gln
            115                 120                 125 caa gtt caa gat ctg gtc att tta gaa agc ata att ttg cag act tta     432
Gln Val Gln Asp Leu Val Ile Leu Glu Ser Ile Ile Leu Gln Thr Leu
        130                 135                 140 ggc ttt gaa cta aca att gat cac cca cat act cat gta gta aag tgc     480
Gly Phe Glu Leu Thr Ile Asp His Pro His Thr His Val Val Lys Cys
145                 150                 155                 160 act caa ctt gtt cga gca agc aag gac tta gca cag act tct tac ttc     528
Thr Gln Leu Val Arg Ala Ser Lys Asp Leu Ala Gln Thr Ser Tyr Phe
               165                 170                 175 atg gca acc aac agc ctg cat ttg acc aca ttt agc ctg cag tac aca     576
Met Ala Thr Asn Ser Leu His Leu Thr Thr Phe Ser Leu Gln Tyr Thr
            180                 185                 190 cct cct gtg gtg gcc tgt gtc tgc att cac ctg gct tgc aag tgg tcc     624
```

-continued

```
Pro Pro Val Val Ala Cys Val Cys Ile His Leu Ala Cys Lys Trp Ser
        195                 200                 205 aat tgg gag atc cca gtc tca act gac ggg aag cac tgg tgg gag tat      672
Asn Trp Glu Ile Pro Val Ser Thr Asp Gly Lys His Trp Trp Glu Tyr
210                 215                 220 gtt gac gcc act gtg acc ttg gaa ctt tta gat gaa ctg aca cat gag      720
Val Asp Ala Thr Val Thr Leu Glu Leu Leu Asp Glu Leu Thr His Glu
225                 230                 235                 240 ttt cta cag att ttg gag aaa act ccc aac agg ctc aaa cgc att tgg      768
Phe Leu Gln Ile Leu Glu Lys Thr Pro Asn Arg Leu Lys Arg Ile Trp
            245                 250                 255 aat tgg agg gca tgc gag gct gcc aag aaa aca aaa gca gat gac cga      816
Asn Trp Arg Ala Cys Glu Ala Ala Lys Lys Thr Lys Ala Asp Asp Arg
            260                 265                 270 gga aca gat gaa aag act tca gag cag aca atc ctc aat atg att tcc      864
Gly Thr Asp Glu Lys Thr Ser Glu Gln Thr Ile Leu Asn Met Ile Ser
        275                 280                 285 cag agc tct tca gac aca acc att gca ggt tta atg agc atg tca act      912
Gln Ser Ser Ser Asp Thr Thr Ile Ala Gly Leu Met Ser Met Ser Thr
    290                 295                 300 tct acc aca agt gca gtg cct tcc ctg cca gtc tcc gaa gag tca tcc      960
Ser Thr Thr Ser Ala Val Pro Ser Leu Pro Val Ser Glu Glu Ser Ser
305                 310                 315                 320 agc aac tta acc agt gtg gag atg ttg ccg ggc aag cgt tgg ctg tcc     1008
Ser Asn Leu Thr Ser Val Glu Met Leu Pro Gly Lys Arg Trp Leu Ser
            325                 330                 335 tcc caa cct tct ttc aaa cta gaa cct act cag ggt cat cgg act agt     1056
Ser Gln Pro Ser Phe Lys Leu Glu Pro Thr Gln Gly His Arg Thr Ser
            340                 345                 350 gag aat tta gca ctt aca gga gtt gat cat tcc tta cca cag gat ggt     1104
Glu Asn Leu Ala Leu Thr Gly Val Asp His Ser Leu Pro Gln Asp Gly
        355                 360                 365 tca aat gca ttt att tcc cag aag cag aat agt aag agt gtg cca tca     1152
Ser Asn Ala Phe Ile Ser Gln Lys Gln Asn Ser Lys Ser Val Pro Ser
    370                 375                 380 gct aaa gtg tca ctg aaa gaa tac cgc gcg aag cat gca gaa gaa ttg     1200
Ala Lys Val Ser Leu Lys Glu Tyr Arg Ala Lys His Ala Glu Glu Leu
385                 390                 395                 400 gct gcc cag aag agg caa ctg gag aac atg gaa gcc aat gtg aag tca     1248
Ala Ala Gln Lys Arg Gln Leu Glu Asn Met Glu Ala Asn Val Lys Ser
            405                 410                 415 caa tat gca tat gct gcc cag aat ctc ctt tct cat cat gat agc cat     1296
Gln Tyr Ala Tyr Ala Ala Gln Asn Leu Leu Ser His His Asp Ser His
            420                 425                 430 tct tca gtc att cta aaa atg ccc ata gag ggt tca gaa aac ccc gag     1344
Ser Ser Val Ile Leu Lys Met Pro Ile Glu Gly Ser Glu Asn Pro Glu
        435                 440                 445 cgg cct ttt ctg gaa aag gct gac aaa aca gct ctc aaa atg aga atc     1392
Arg Pro Phe Leu Glu Lys Ala Asp Lys Thr Ala Leu Lys Met Arg Ile
    450                 455                 460 cca gtg gca ggt gga gat aaa gct gcg tct tca aaa cca gag gag ata     1440
Pro Val Ala Gly Gly Asp Lys Ala Ala Ser Ser Lys Pro Glu Glu Ile
465                 470                 475                 480 aaa atg cgc ata aaa gtc cat gct gca gct gat aag cac aat tct gta     1488
Lys Met Arg Ile Lys Val His Ala Ala Ala Asp Lys His Asn Ser Val
            485                 490                 495 gag gac agt gtt aca aag agc cga gag cac aaa gaa aag cac aag act     1536
Glu Asp Ser Val Thr Lys Ser Arg Glu His Lys Glu Lys His Lys Thr
        500                 505                 510
```

-continued

```
cac cca tct aat cat cat cat cat aat cac cac tca cac aag cac      1584
His Pro Ser Asn His His His His Asn His His Ser His Lys His
        515                 520                 525 tct cat tcc caa ctt cca gtt ggt act ggg aac aaa cgt cct ggt gat  1632
Ser His Ser Gln Leu Pro Val Gly Thr Gly Asn Lys Arg Pro Gly Asp
    530                 535                 540 cca aaa cat agt agc cag aca agc aac tta gca cat aaa acc tat agc  1680
Pro Lys His Ser Ser Gln Thr Ser Asn Leu Ala His Lys Thr Tyr Ser
545                 550                 555                 560 ttg tct agt tct ttt tcc tct tcc agt tct act cgt aaa agg gga ccc  1728
Leu Ser Ser Ser Phe Ser Ser Ser Ser Ser Thr Arg Lys Arg Gly Pro
                565                 570                 575 tct gaa gag act gga ggg gct gtg ttt gat cat cca gcc aag att gcc  1776
Ser Glu Glu Thr Gly Gly Ala Val Phe Asp His Pro Ala Lys Ile Ala
            580                 585                 590 aag agt act aaa tcc tct tcc cta aat ttc tcc ttc cct tca ctt cct  1824
Lys Ser Thr Lys Ser Ser Ser Leu Asn Phe Ser Phe Pro Ser Leu Pro
        595                 600                 605 aca atg ggt cag atg cct ggg cat agc tca gac aca agt ggc ctt tcc  1872
Thr Met Gly Gln Met Pro Gly His Ser Ser Asp Thr Ser Gly Leu Ser
    610                 615                 620 ttt tca cag ccc agc tgt aaa act cgt gtc cct cat tcg aaa ctg gat  1920
Phe Ser Gln Pro Ser Cys Lys Thr Arg Val Pro His Ser Lys Leu Asp
625                 630                 635                 640 aaa ggg ccc act ggg gcc aat ggt cac aac acg acc cag aca ata gac  1968
Lys Gly Pro Thr Gly Ala Asn Gly His Asn Thr Thr Gln Thr Ile Asp
                645                 650                 655 tat caa gac act gtg aat atg ctt cac tcc ctg ctc agt gcc cag ggt  2016
Tyr Gln Asp Thr Val Asn Met Leu His Ser Leu Leu Ser Ala Gln Gly
            660                 665                 670 gtt cag ccc act cag cct act gca ttt gaa ttt gtt cgt cct tat agt  2064
Val Gln Pro Thr Gln Pro Thr Ala Phe Glu Phe Val Arg Pro Tyr Ser
        675                 680                 685 gac tat ctg aat cct cgg tct ggt gga atc tcc tcg aga tct ggc aat  2112
Asp Tyr Leu Asn Pro Arg Ser Gly Gly Ile Ser Ser Arg Ser Gly Asn
    690                 695                 700 aca gac aaa ccc cgg cca cca cct ctg cca tca gaa cct cct cca cca  2160
Thr Asp Lys Pro Arg Pro Pro Pro Leu Pro Ser Glu Pro Pro Pro Pro
705                 710                 715                 720 ctt cca ccc ctt cct aag taa                                      2181
Leu Pro Pro Leu Pro Lys
                725

<210> SEQ ID NO 2
<211> LENGTH: 726
<212> TYPE: PRT
<213> ORGANISM: Homo sapiens

<400> SEQUENCE: 2

Met Glu Gly Glu Arg Lys Asn Asn Asn Lys Arg Trp Tyr Phe Thr Arg
1               5                   10                  15

Glu Gln Leu Glu Asn Ser Pro Ser Arg Arg Phe Gly Val Asp Pro Asp
            20                  25                  30

Lys Glu Leu Ser Tyr Arg Gln Gln Ala Ala Asn Leu Leu Gln Asp Met
        35                  40                  45

Gly Gln Arg Leu Asn Val Ser Gln Leu Thr Ile Asn Thr Ala Ile Val
    50                  55                  60

Tyr Met His Arg Phe Tyr Met Ile Gln Ser Phe Thr Gln Phe Pro Gly
65                  70                  75                  80
```

```
Asn Ser Val Ala Pro Ala Ala Leu Phe Leu Ala Ala Lys Val Glu Glu
                 85                  90                  95

Gln Pro Lys Lys Leu Glu His Val Ile Lys Val Ala His Thr Cys Leu
            100                 105                 110

His Pro Gln Glu Ser Leu Pro Asp Thr Arg Ser Glu Ala Tyr Leu Gln
            115                 120                 125

Gln Val Gln Asp Leu Val Ile Leu Glu Ser Ile Ile Leu Gln Thr Leu
        130                 135                 140

Gly Phe Glu Leu Thr Ile Asp His Pro His Thr His Val Val Lys Cys
145                 150                 155                 160

Thr Gln Leu Val Arg Ala Ser Lys Asp Leu Ala Gln Thr Ser Tyr Phe
                165                 170                 175

Met Ala Thr Asn Ser Leu His Leu Thr Thr Phe Ser Leu Gln Tyr Thr
                180                 185                 190

Pro Pro Val Val Ala Cys Val Cys Ile His Leu Ala Cys Lys Trp Ser
            195                 200                 205

Asn Trp Glu Ile Pro Val Ser Thr Asp Gly Lys His Trp Trp Glu Tyr
        210                 215                 220

Val Asp Ala Thr Val Thr Leu Glu Leu Leu Asp Glu Leu Thr His Glu
225                 230                 235                 240

Phe Leu Gln Ile Leu Glu Lys Thr Pro Asn Arg Leu Lys Arg Ile Trp
                245                 250                 255

Asn Trp Arg Ala Cys Glu Ala Ala Lys Lys Thr Lys Ala Asp Asp Arg
                260                 265                 270

Gly Thr Asp Glu Lys Thr Ser Glu Gln Thr Ile Leu Asn Met Ile Ser
            275                 280                 285

Gln Ser Ser Asp Thr Thr Ile Ala Gly Leu Met Ser Met Ser Thr
        290                 295                 300

Ser Thr Thr Ser Ala Val Pro Ser Leu Pro Val Ser Glu Glu Ser Ser
305                 310                 315                 320

Ser Asn Leu Thr Ser Val Glu Met Leu Pro Gly Lys Arg Trp Leu Ser
                325                 330                 335

Ser Gln Pro Ser Phe Lys Leu Glu Pro Thr Gln Gly His Arg Thr Ser
            340                 345                 350

Glu Asn Leu Ala Leu Thr Gly Val Asp His Ser Leu Pro Gln Asp Gly
        355                 360                 365

Ser Asn Ala Phe Ile Ser Gln Lys Gln Asn Ser Lys Ser Val Pro Ser
    370                 375                 380

Ala Lys Val Ser Leu Lys Glu Tyr Arg Ala Lys His Ala Glu Glu Leu
385                 390                 395                 400

Ala Ala Gln Lys Arg Gln Leu Glu Asn Met Glu Ala Asn Val Lys Ser
                405                 410                 415

Gln Tyr Ala Tyr Ala Ala Gln Asn Leu Leu Ser His His Asp Ser His
            420                 425                 430

Ser Ser Val Ile Leu Lys Met Pro Ile Glu Gly Ser Glu Asn Pro Glu
        435                 440                 445

Arg Pro Phe Leu Glu Lys Ala Asp Lys Thr Ala Leu Lys Met Arg Ile
    450                 455                 460

Pro Val Ala Gly Gly Asp Lys Ala Ala Ser Ser Lys Pro Glu Glu Ile
465                 470                 475                 480

Lys Met Arg Ile Lys Val His Ala Ala Asp Lys His Asn Ser Val
                485                 490                 495

Glu Asp Ser Val Thr Lys Ser Arg Glu His Lys Glu Lys His Lys Thr
```

-continued

```
                   500                 505                 510
        His Pro Ser Asn His His His Asn His Ser His Lys His
                    515                 520                 525
        Ser His Ser Gln Leu Pro Val Gly Thr Gly Asn Lys Arg Pro Gly Asp
                    530                 535                 540
        Pro Lys His Ser Ser Gln Thr Ser Asn Leu Ala His Lys Thr Tyr Ser
        545                 550                 555                 560
        Leu Ser Ser Ser Phe Ser Ser Ser Ser Thr Arg Lys Arg Gly Pro
                        565                 570                 575
        Ser Glu Glu Thr Gly Gly Ala Val Phe Asp His Pro Ala Lys Ile Ala
                    580                 585                 590
        Lys Ser Thr Lys Ser Ser Ser Leu Asn Phe Ser Phe Pro Ser Leu Pro
                    595                 600                 605
        Thr Met Gly Gln Met Pro Gly His Ser Ser Asp Thr Ser Gly Leu Ser
                    610                 615                 620
        Phe Ser Gln Pro Ser Cys Lys Thr Arg Val Pro His Ser Lys Leu Asp
        625                 630                 635                 640
        Lys Gly Pro Thr Gly Ala Asn Gly His Asn Thr Thr Gln Thr Ile Asp
                        645                 650                 655
        Tyr Gln Asp Thr Val Asn Met Leu His Ser Leu Leu Ser Ala Gln Gly
                    660                 665                 670
        Val Gln Pro Thr Gln Pro Thr Ala Phe Glu Phe Val Arg Pro Tyr Ser
                    675                 680                 685
        Asp Tyr Leu Asn Pro Arg Ser Gly Gly Ile Ser Ser Arg Ser Gly Asn
                    690                 695                 700
        Thr Asp Lys Pro Arg Pro Pro Leu Pro Ser Glu Pro Pro Pro
        705                 710                 715                 720
        Leu Pro Pro Leu Pro Lys
                        725
```

```
<210> SEQ ID NO 3
<211> LENGTH: 17
<212> TYPE: DNA
<213> ORGANISM: Artificial Sequence
<220> FEATURE:
<223> OTHER INFORMATION: oligonucleotide for PCR

<400> SEQUENCE: 3
cggaggactg tcctccg                                                   17

<210> SEQ ID NO 4
<211> LENGTH: 22
<212> TYPE: DNA
<213> ORGANISM: Artificial Sequence
<220> FEATURE:
<223> OTHER INFORMATION: oligonucleotide for PCR

<400> SEQUENCE: 4
ggaaaaggct gacaaaacag ct                                             22

<210> SEQ ID NO 5
<211> LENGTH: 29
<212> TYPE: DNA
<213> ORGANISM: Artificial Sequence
<220> FEATURE:
<223> OTHER INFORMATION: oligonucleotide for PCR

<400> SEQUENCE: 5
cggaattcgg caggtggaga taaagctgc                                      29
```

<210> SEQ ID NO 6
<211> LENGTH: 129
<212> TYPE: PRT
<213> ORGANISM: Caenorhabditis elegans

<400> SEQUENCE: 6

Lys Trp Leu Phe Thr Lys Glu Glu Met Lys Lys Thr Ala Ser Ile Gln
 1               5                  10                  15

Glu Gly Met Ser Arg Glu Glu Leu Ala Ser Arg Gln Met Ala Ala
            20                  25                  30

Ala Phe Ile Gln Glu Met Ile Asp Gly Leu Asn Ile Gly His Thr Gly
        35                  40                  45

Leu Cys Val Ala His Thr His Met His Arg Phe Tyr Tyr Leu His Ser
    50                  55                  60

Phe Lys Lys Tyr Asp Tyr Arg Asp Val Gly Ala Ala Cys Val Phe Leu
65                  70                  75                  80

Ala Gly Lys Ser Gln Glu Cys Pro Arg Lys Leu Ser His Val Ile Ser
                85                  90                  95

Val Trp Arg Glu Arg Lys Asp Arg Lys Gln Leu Asn Asn Asn Thr Thr
            100                 105                 110

Glu Thr Ala Arg Asn Glu Ala Ala Gln Ile Ile Val Leu Leu Glu Ser
        115                 120                 125

Met

<210> SEQ ID NO 7
<211> LENGTH: 129
<212> TYPE: PRT
<213> ORGANISM: Schizosaccharomyces pombe
<220> FEATURE:
<221> NAME/KEY: VARIANT
<222> LOCATION: (1)...(129)
<223> OTHER INFORMATION: Xaa = Any Amino Acid

<400> SEQUENCE: 7

Gln Trp Ile Ile Ser Lys Asp Gln Leu Val Thr Phe Pro Ser Ala Leu
 1               5                  10                  15

Asp Gly Ile Pro Leu Asp Gln Glu Ile Gln Arg Ser Lys Gly Cys
            20                  25                  30

Asn Phe Ile Ile Asn Val Gly Leu Arg Leu Lys Leu Pro Gln Thr Ala
        35                  40                  45

Leu Ala Thr Ala Asn Ile Tyr Phe His Arg Phe Tyr Leu Arg Phe Ser
    50                  55                  60

Leu Lys Asn Tyr His Tyr Tyr Glu Val Ala Ala Thr Cys Ile Phe Leu
65                  70                  75                  80

Ala Thr Lys Val Glu Asp Ser Val Arg Lys Leu Arg Asp Ile Val Ile
                85                  90                  95

Asn Cys Ala Lys Val Ala Gln Lys Asn Ser Asn Val Leu Val Asp Glu
            100                 105                 110

Gln Thr Lys Glu Tyr Trp Arg Trp Arg Asp Xaa Val Ile Leu Tyr Thr
        115                 120                 125

Glu

<210> SEQ ID NO 8
<211> LENGTH: 129
<212> TYPE: PRT
<213> ORGANISM: Homo sapiens

<400> SEQUENCE: 8

```
Tyr Leu Gln Trp Ile Leu Asp Lys Gln Asp Leu Leu Lys Glu Arg Gln
 1               5                  10                  15
Lys Asp Leu Lys Phe Leu Ser Glu Glu Glu Tyr Trp Lys Leu Gln Ile
             20                  25                  30
Phe Phe Thr Asn Val Ile Gln Ala Leu Gly Glu Leu Arg Gln Gln Val
         35                  40                  45
Ile Ala Thr Ala Thr Val Tyr Phe Lys Arg Phe Tyr Ala Arg Tyr Ser
 50                  55                  60
Leu Lys Ser Ile Asp Pro Val Leu Met Ala Pro Thr Cys Val Phe Leu
 65                  70                  75                  80
Ala Ser Lys Val Glu Glu Phe Gly Val Val Ser Asn Thr Arg Leu Ile
                 85                  90                  95
Ala Ala Ala Thr Ser Val Leu Lys Thr Arg Phe Ser Tyr Ala Phe Pro
            100                 105                 110
Lys Glu Phe Pro Tyr Arg Met Asn His Ile Leu Glu Cys Glu Phe Tyr
            115                 120                 125
Leu
```

<210> SEQ ID NO 9
<211> LENGTH: 131
<212> TYPE: PRT
<213> ORGANISM: Homo sapiens

<400> SEQUENCE: 9

```
Phe Arg Cys Lys Ala Val Ala Asn Gly Lys Val Leu Pro Asn Asp Pro
 1               5                  10                  15
Val Phe Leu Glu Pro His Glu Glu Met Thr Leu Cys Lys Tyr Tyr Glu
             20                  25                  30
Lys Arg Leu Leu Glu Phe Cys Ser Val Phe Lys Pro Ala Met Pro Arg
         35                  40                  45
Ser Val Val Gly Thr Ala Cys Met Tyr Phe Lys Arg Phe Tyr Leu Asn
 50                  55                  60
Asn Ser Val Met Glu Tyr His Pro Arg Ile Ile Met Leu Thr Cys Ala
 65                  70                  75                  80
Phe Leu Ala Cys Lys Val Asp Glu Phe Asn Val Ser Ser Pro Gln Phe
                 85                  90                  95
Val Gly Asn Leu Arg Glu Ser Pro Leu Gly Gln Glu Lys Ala Leu Glu
            100                 105                 110
Gln Ile Leu Glu Tyr Glu Leu Leu Leu Ile Gln Gln Leu Asn Phe His
            115                 120                 125
Leu Ile Val
        130
```

<210> SEQ ID NO 10
<211> LENGTH: 21
<212> TYPE: RNA
<213> ORGANISM: Homo sapiens

<400> SEQUENCE: 10
gaucugagcc ugggagcucu c                                     21

<210> SEQ ID NO 11
<211> LENGTH: 11
<212> TYPE: PRT
<213> ORGANISM: Homo sapiens

```
<400> SEQUENCE: 11

Ala Asn Val Asp Pro Asp Leu Glu Leu Ser Tyr
1               5                   10

<210> SEQ ID NO 12
<211> LENGTH: 12
<212> TYPE: PRT
<213> ORGANISM: Homo sapiens

<400> SEQUENCE: 12

Gln Gln Ala Ala Asn Leu Leu Ser Asp Met Gly Gln
1               5                   10

<210> SEQ ID NO 13
<211> LENGTH: 15
<212> TYPE: PRT
<213> ORGANISM: Homo sapiens

<400> SEQUENCE: 13

Thr Ser Glu Asn Leu Ala Leu Thr Gly Val Asp His Ser Leu Pro
1               5                   10                  15

<210> SEQ ID NO 14
<211> LENGTH: 10
<212> TYPE: PRT
<213> ORGANISM: Homo sapiens

<400> SEQUENCE: 14

Gln Leu Glu Asn Met Glu Ala Asn Val Lys
1               5                   10

<210> SEQ ID NO 15
<211> LENGTH: 5
<212> TYPE: PRT
<213> ORGANISM: Homo sapiens

<400> SEQUENCE: 15

Ser Gln Tyr Ala Tyr
1               5

<210> SEQ ID NO 16
<211> LENGTH: 11
<212> TYPE: PRT
<213> ORGANISM: Homo sapiens
<220> FEATURE:
<221> NAME/KEY: VARIANT
<222> LOCATION: 7, 11
<223> OTHER INFORMATION: Xaa = Ser or Cys

<400> SEQUENCE: 16

Ala Ala Gln Asn Leu Leu Xaa His His Asp Xaa
1               5                   10

<210> SEQ ID NO 17
<211> LENGTH: 9
<212> TYPE: PRT
<213> ORGANISM: Homo sapiens
<220> FEATURE:
<221> NAME/KEY: VARIANT
<222> LOCATION: 7
<223> OTHER INFORMATION: Xaa = Any Amino Acid
<220> FEATURE:
<221> NAME/KEY: VARIANT
<222> LOCATION: 9
<223> OTHER INFORMATION: Xaa = Ser or Cys

<400> SEQUENCE: 17
```

```
Gly Tyr Ser Leu Ser Ser Xaa Phe Xaa
1               5

<210> SEQ ID NO 18
<211> LENGTH: 15
<212> TYPE: PRT
<213> ORGANISM: Homo sapiens

<400> SEQUENCE: 18

Gly Pro Ser Glu Glu Thr Gly Gly Ala Val Phe Asp His Pro Ala
1               5                   10                  15

<210> SEQ ID NO 19
<211> LENGTH: 9
<212> TYPE: PRT
<213> ORGANISM: Homo sapiens

<400> SEQUENCE: 19

Ser Gly Asn Thr Asp Lys Pro Arg Pro
1               5
```

TRANSCRIPTIONAL COACTIVATOR THAT INTERACTS WITH TAT PROTEIN AND REGULATES ITS BINDING TO TAR RNA, METHODS FOR MODULATING TAT TRANSACTIVATION, AND USES THEREFOR

RELATED APPLICATIONS

This application claims priority from U.S. Provisional Application No. 60/069,341, filed Dec. 11, 1997, and Continuation-in-Part application Ser. No. 09/126,980, filed Jul. 30, 1998, now pending, each of which is incorporated by reference herein in its entirety.

FIELD OF THE INVENTION

The present invention relates to compounds useful for the modulation of Tat transactivation, methods for the modulation of Tat transactivation and methods for the identification of such compounds.

BACKGROUND OF THE INVENTION

The human immunodeficiency virus (HIV) encodes a nuclear transcriptional activator, Tat, which acts to enhance the processivity of RNA polymerase II (RNAPII) complexes that would otherwise terminate transcription prematurely at random locations downstream of the viral RNA start site. The mechanism of Tat transactivation is unique in that the cis-acting transactivation response element (TAR) is a stable RNA stem-loop structure that forms at the 5' end of nascent viral transcripts. Transcriptional activation by Tat through TAR requires proper folding of the RNA as well as specific bases in the bulge and apical loop of the TAR RNA hairpin structure (for review, see Cullen, B. (1993) Cell 73:417–420; Jones and Peterlin (1994) Annu Rev Biochem 63:717–743).

The interaction of Tat with TAR RNA is mediated through an arginine-rich motif (ARM) that is characteristic of a family of sequence-specific RNA-binding proteins (Gait and Karn (1993) Trends Biochem Sci 18:255–259). However, several lines of evidence suggest that the ARM of Tat is not an independent domain. First, the transactivation domain of Tat cannot be substituted by the activation domains of other transcription factors, such as the herpes virus VP16 protein, even though the VP16 activation domain is capable of activating transcription when tethered to RNA through a different RNA-binding domain (Tiley et al. (1992) Genes Dev 6:2077–2087; Ghosh et al. (1993) J Mol Biol 234:610–619). Second, the full-length Tat-1 protein, but not a mutant Tat protein that retains the ARM but lacks the transactivation domain, is able to target a heterologous protein to TAR RNA in vivo (Luo et al. (1993) J Virol 67:5617–5622), indicating that the activation domain is required to target Tat to TAR in the cell. Third, amino acid insertions that separate the Tat activation domain from the ARM strongly reduce transactivation through TAR, but do not affect TAR-independent transactivation by chimeric Tat proteins (Luo and Peterlin (1993) J Virol 67:3441–3445). Fourth, over-expression of mutant Tat proteins that contain the ARM does not block transactivation by the wild-type Tat protein in vivo (Madore and Cullen (1993) J Virol 67:3703–3711). In addition, residues in the core of the transactivation domain have been found to enhance the affinity and specificity of the Tat:TAR interaction in vitro (Churcher et al. (1993) J Mol Biol 230:90–110). Taken together, these studies strongly suggest that amino acid residues within the transactivation domain are required, directly or indirectly, for efficient binding of Tat to TAR RNA in vivo.

Tat recognizes a specific sequence in TAR that forms between the bulge and the upper stem, but does not require sequences in the loop of the hairpin that are essential for transactivation both in vivo and in vitro (for review, see Gait and Karn (1993) Trends Biochem Sci 18:255–259). Based on these findings, it has been postulated that Tat must interact with a host cell RNA-binding cofactor in order to recognize TAR RNA with high affinity and in a sequence-appropriate manner. Consistent with this possibility, it has been shown that high levels of Tat cannot overcome the specific inhibition of transactivation that occurs when cells are exposed to high levels of exogenous synthetic TAR "decoy" RNAs (Sullenger et al. (1990) Cell 63:601–608, Sullenger et al. (1991) J Virol 65:6811–6816; Bohjanen et al. (1996) Nucl Acids Res 24:3733–3738). Thus exogenous TAR RNAs appear to sequester a cellular cofactor in addition to Tat. Moreover, genetic studies indicate that a species-specific host cell factor is necessary for Tat to activate transcription through TAR in vivo. In particular, it has been found that murine and Chinese hamster ovary (CHO) cell lines do not support efficient transcription by Tat through TAR RNA (Hart et al. (1989) Science 246:488–491; Newstein et al. (1990) J Virol 64:4565–4567), whereas these same cell lines can support TAR-independent transactivation by chimeric Tat proteins (e.g., GAL4-Tat, Rev-Tat, MS2CP-Tat) that are targeted to their responsive promoters through a heterologous DNA- or RNA-binding domain (Alonso et al. (1992) J Virol 66:4617–4621; Newstein et al. (1993) Virol 197:825–828). Therefore the defect in nonpermissive rodent cells appears to be due to a problem of TAR RNA recognition.

Analysis of human:CHO hybrid cell clones reveals that a factor encoded on human chromosome 12 (Chr 12) can support a modest level of Tat activity in rodent cells (Hart et al. (1989) Science 246:488–491; Newstein et al. (1990) J Virol 64:4565–4567), and, most importantly, that the chromosome 12-encoded factor confers a specific requirement for sequences in the loop of TAR RNA that are otherwise dispensable for the residual low-level Tat activity that is observed in rodent cells (Alonso et al. (1994) J Virol 66:6505–6513; Hart et al. (1993) J Virol 67:5020–5024; Sutton et al. (1995) Virol 206:690–694). UV cross-linking studies have identified a cellular 83 kDa RNA-binding protein that is present in human and CHO-Chr12 cells, but not in CHO cells, which binds to TAR RNA in a loop-dependent manner (Hart et al. (1995) J Virol 69:6593–6599). Taken together, these results suggest that a human species-specific factor mediates the high-affinity, loop-specific binding of Tat to TAR RNA in vivo.

It has been generally presumed that the TAR RNA-binding cofactor would be distinct from the transcriptional coactivator for Tat. By contrast with the ARM, the N-terminal half of Tat can function autonomously as a transcriptional activation domain when fused to the DNA- or RNA-binding domain of a heterologous protein and targeted to an appropriate promoter. Truncated Tat-1 proteins that contain only the transactivation domain (aa 1–48) also act as potent dominant negative inhibitors of the wild-type HIV-1, HIV-2 and EIAV (equine infectious anemia virus) Tat proteins, suggesting that this region of Tat can sequester a limiting host cell transcription factor(s) that is necessary for Tat transactivation. Tat controls an early step in transcription elongation that is sensitive to inhibition by protein kinase inhibitors such as 5,6-dichloro-1-b-D-ribofuranosylbenzimidazole (DRB) (Kao et al. (1987) Nature 330:489–493; Laspia et al. (1993) J Mol Biol 232:732–746; Marciniak et al. (1990) Cell 63:791–802;

Marciniak and Sharp (1991) *EMBO J* 10:4189–4196), and Tat transactivation in vivo and in vitro requires the carboxyl-terminal domain (CTD) of the largest subunit of RNA polymerase II (Chun and Jeang (1996) *J Biol Chem* 271:27888–27894; Okamoto et al. (1996)*Proc Natl Acad Sci USA* 93:11575–11579; Parada and Roeder (1996) *Nature* 384:375–378; Yang et al. (1996) *J Virol* 70:4576–4584).

The RNAPII carboxyl-terminal domain is predominantly unphosphorylated in assembled RNAPII preinitiation complexes and in complexes that pause shortly after initiation, but becomes heavily phosphorylated upon entry into productive elongation (for review, see Dahmus, M. (1996) *J Biol Chem* 271:19009–19012). Although the carboxyl-terminal domain is critical for gene expression in vivo and for regulated transcription in crude extracts, it is not required for basal promoter activity in purified reconstituted transcription systems (Serizawa et al. (1993) *Nature* 363:371–374). For many genes, the carboxyl-terminal domain has been found to be significantly more important for elongation than for initiation, which provides further support for the notion that carboxyl-terminal domain hyperphosphorylation may be an important step marking the transition of RNAPII molecules to forms that are competent for elongation (for review see Maldonado and Reinberg (1995) *Curr Opin Cell Biol* 7:352–361; Shilatifard et al. (1997) *Curr Opin Genet Dev* 7:199–204). The available evidence indicates that Tat acts through TAR RNA to regulate this DRB-sensitive, carboxyl-terminal domain kinase-dependent step in early elongation at the HIV-1 promoter (for review, see Jones, K A (1997) *Genes Dev* 11:2593–2599).

The possibility that Tat might interfere directly with a carboxyl-terminal domain kinase was first suggested by the finding that both HIV-1 and HIV-2 Tat proteins interact very strongly, in vitro and in vivo, with a nuclear protein kinase (Herrmann and Rice (1993) *Virol* 197:601–608). Highly enriched fractions of the Tat-associated kinase (TAK) were shown to support hyperphosphorylation of the RNAPII carboxyl-terminal domain in vitro (Herrmann and Rice (1995) *J Virol* 69:1612–1620). Recently, the catalytic subunit of TAK was shown to be identical to a protein kinase subunit of P-TEFb, a RNAPII positive-acting transcription elongation factor complex that was purified originally from Drosophila cell transcription extracts (Mancebo et al. (1997) *Genes Dev* 11:2633–2644; Zhu et al. (1997) *Genes Dev* 11:2622–2632). Sequence analysis of the catalytic subunit of Drosophila P-TEFb establish its near identity to the human CDC2-related kinase, PITALRE, and the PITALRE kinase (hereafter called CDK9) has been shown to be critical for both TAK and P-TEFb activity (Mancebo et al. (1997) *Genes Dev* 11:2633–2644; Yang et al. (1997) *Proc Natl Acad Sci USA* 94:12331–12336; Zhu et al. (1997) *Genes Dev* 11:2622–2632). Immunoprecipitation of CDK9 from HeLa nuclear extracts effectively inhibits transcription elongation in vitro, and the residual transcription that remains is no longer sensitive to inhibition by DRB (Zhu et al. (1997) *Genes Dev* 11:2622–2632).

Independent support for a role for CDK9 in Tat transactivation comes from random drug screens for specific inhibitors of Tat, which yield novel compounds directed against the active site of CDK9 (Mancebo et al. (1997) *Genes Dev* 11:2633–2644), and the demonstration that a dominant negative mutant CDK9 protein blocks Tat activity in vivo (Mancebo et al. (1997) *Genes Dev* 11:2633–2644; Yang et al. (1997) *Proc Natl Acad Sci USA* 94:12331–12336). Interestingly, purified Drosophila P-TEFb is able to restore general transcription elongation to HeLa extracts that have been depleted of CDK9, but is unable to restore transactivation by Tat (Mancebo et al. (1997) *Genes Dev* 11:2633–2644; Zhu et al. (1997) *Genes Dev* 11:2622–2632), indicating that human-specific proteins associated with CDK9 may be necessary for Tat activity.

The human immunodeficiency virus (HIV-1) Tat protein is a potent activator of HIV-1 transcription that functions at an early step in elongation. Accordingly, there is a need in the art for a further understanding of the interaction(s) between the various components involved in Tat transactivation. A clearer understanding of these processes will facilitate the development of methods to modulate Tat transactivation, as well as assays for the identification of compounds useful for such modulation. These and other needs in the art are addressed by the present invention.

BRIEF DESCRIPTION OF THE INVENTION

In accordance with the present invention, a host cell protein has been discovered which regulates Tat transactivation. The protein is the first discovered constituent of the TAK/TEFb complex which associates with the HIV Tat, and is necessary for the binding of Tat to TAR RNA. This protein, cyclin T1, an 87 kDa cyclin partner for the PITALRE kinase, is believed to associate with the HIV Tat via divalent cation metals. It has further been discovered that Tat must interact with TAK in order to bind to TAR RNA with affinity and with the appropriate sequence specificity that is observed in vivo.

In accordance with another aspect of the invention, formulations useful for modulation of Tat transactivation have been developed. In addition, assays have been developed for the identification of compounds useful to modulate the above-described processes.

BRIEF DESCRIPTION OF THE FIGURES

FIG. 1(B) provides a sequence alignment of human cyclin T1 with *C. elegans* YL34 (SEQ ID NO:6), *S. pombe* Pch1(+) (SEQ ID NO:7), human cyclin C (SEQ ID NO:8) and human cyclin H (SEQ ID NO:9). Shaded boxes indicate the location of cyclin helices in the predicted structure of human cyclin H.

DETAILED DESCRIPTION OF THE INVENTION

Figure 1A:
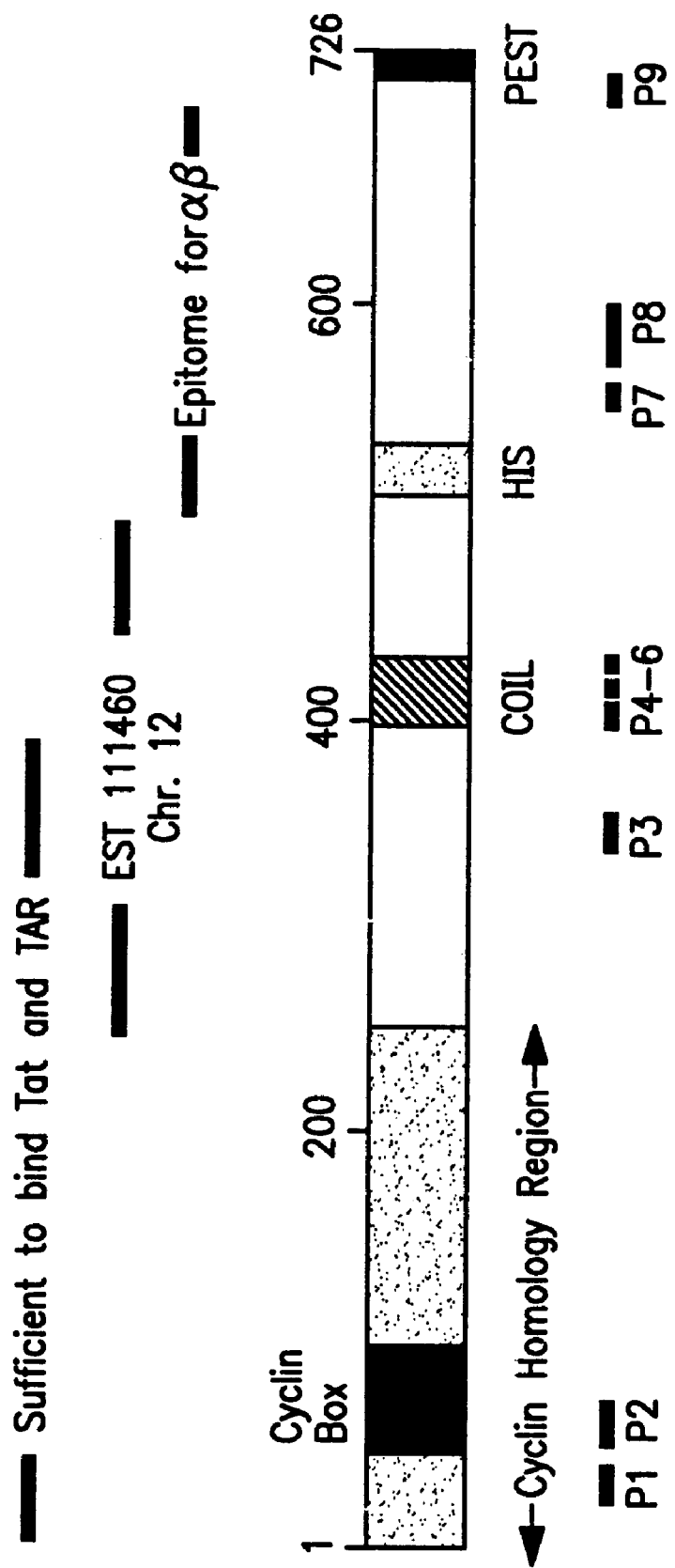
FIG. 1(A) provides a schematic representation of putative structural domains of the human cyclin T1 protein, indicating the region contained within the EST clone 111460 and the region used as an epitope for antibody production. Darker shaded area in the region of homology to C-type cyclins represents the cyclin box. The location of the nine tryptic fragments (P1 to P9) derived from microsequencing of purified HeLa p87 are underlined below the diagram.

In accordance with the present invention, it has been discovered that HIV Tat and a nuclear carboxyl-terminal domain kinase, TAK/TEFb, form a complex to associate with TAR RNA in a loop-specific manner. It has also been discovered that 1) the RNA-binding activity of uncomplexed Tat is negatively regulated by the amino terminal half of the Tat protein, 2) full-length HIV-1 and HIV-2 Tat proteins interact much more strongly with TAR-2 than with TAR-1 RNA, and that optimal binding of Tat to TAR-2 RNA requires sequence in the loop of the RNA hairpin, 3) the transactivation domain of Tat contributes significantly to the specificity of the Tat:TAR interaction, and in particular is required for-loop specific binding to TAR-2, and 4) Tat must interact with the multisubunit transcription elongation factor (TAK/TEFb) complex to bind to TAR-1 and TAR-2 with high affinity and with the appropriate sequence specificity that is observed in vivo. Taken together, these discoveries strongly implicate TAK/P-TEFb as the host cell transcriptional coactivator and TAR RNA-binding cofactor for Tat.

In accordance with the present invention, there are provided isolated Tat-associating polyeptide(s), or functional fragments thereof, wherein the polypeptide is a constituent of the TAK/TEFb complex and, wherein the polypeptide modulates Tat transactivation by enhancing the affinity of the Tat protein with TAR RNA. An isolated polypeptide in the TAK/TEFb complex that interacts with the transactivation domain of Tat is the human 87 kDa cyclin C-related protein, cyclin T1 (also called cyclin K). It has recently been found that the binding of HIV-1 Tat to human cyclin T requires the presence of divalent cation metals. Divalent cation metals, such as zinc, cadmium, iron, and the like, are required for the proteins to bind to each other and to form a stable complex on TAR RNA. Recent studies suggest that divalent cation metals, particularly zinc, form a bridge that connects Tat with the cyclin T protein through cysteine residues in both Tat and cyclin T1.

Cyclin T1, encoded on human chromosome 12, is the cyclin partner for CDK9. Microsequencing of cyclin T1 yields 9 peptides and reveals several domains including a cyclin groove, an N-terminal cyclin box (amino acid sequence 35–85 as set forth in SEQ ID NO:2), a coiled-coil motif representative of protein interaction domains of other proteins, a histidine rich motif, several cysteine residues (i.e., cysteine at amino acid residue 261, as set forth in SEQ ID NO:2) which are capable of binding divalent cation metals, such as zinc, cadmium, and the like, and a C-terminal PEST motif which targets proteins for degradation (amino acid sequence 697–725 as set forth in SEQ ID NO:2). In a preferred aspect of the invention, there are provided polypeptides comprising substantially the same amino acid sequence as set forth in SEQ ID NO:2, or functional fragments thereof (for example, a fragment comprising the amino acid residues 1–380 as set forth in SEQ ID NO:2).

Alternatively, there are provided isolated Tat-associating peptides, polypeptides(s) and/or protein(s), or fragments thereof, encoded by nucleic acid that hybridizes, under low stringency conditions, preferably moderate stringency conditions to substantially the entire nucleic acid sequence as set forth in SEQ ID NO:1, or substantial portions thereof (i.e., zinc/Tat interaction domain, cyclin groove, CDK binding domain, nucleotides 1–1440 as set forth in SEQ ID NO:1, and the like). The term "nucleic acids" (also referred to as nucleotides) encompasses RNA as well as single and double-stranded DNA and cDNA.

As used herein, the term "isolated," with respect to polypeptides, means a protein molecule free of cellular components and/or contaminants normally associated with a native in vivo environment. Invention polypeptides and/or proteins include any isolated naturally occurring allelic variant, as well as recombinant forms thereof. Invention polypeptides can be isolated using various methods well known to those of skill in the art. The methods available for the isolation and purification of invention proteins include, precipitation, gel filtration, ion-exchange, reverse-phase and affinity chromatography, and the like. Other well-known methods are described in Deutscher et al., *Guide to Protein Purification: Methods in Enzymology* Vol. 182, (Academic Press, (1990)), which is incorporated herein by reference. Alternatively, the isolated polypeptides of the present invention can be obtained using well-known recombinant methods as described, for example, in Sambrook et al., supra., 1989).

As used herein, the phrase "isolated nucleic acid" means a nucleic acid that is in a form that does not occur in nature. One means of isolating a nucleic acid encoding a polypeptide is to probe a mammalian genomic library with a natural or artificially designed DNA probe using methods well known in the art. DNA probes derived from the cyclin T1 gene are particularly useful for this purpose. DNA and cDNA molecules that encode cyclin T1 polypeptides can be used to obtain complementary genomic DNA, cDNA or RNA from human, mammalian (e.g., mouse, rat, rabbit, pig, and the like), or other animal sources, or to isolate related cDNA or genomic clones by the screening of cDNA or genomic libraries, by methods described in more detail below. Examples of nucleic acids are RNA, cDNA, or isolated genomic DNA encoding a cyclin T1 polypeptide. Such nucleic acids may include, but are not limited to, nucleic acids having substantially the same nucleotide sequence set forth in SEQ ID NO:1, or at least nucleotides 1–1440 of SEQ ID NO:1.

The phrase "substantially the same" is used herein in reference to the nucleotide sequence of DNA, the ribonucleotide sequence of RNA, or the amino acid sequence of protein, and embraces sequences that have slight and non-consequential sequence variations from the actual sequences disclosed herein. Species that are substantially the same are considered to be equivalent to the disclosed sequences and as such are within the scope of the appended claims. In this regard, "slight and non-consequential sequence variations" mean that sequences that are substantially the same as the DNA, RNA, or proteins disclosed and claimed herein are functionally equivalent to the sequences disclosed and claimed herein. Functionally equivalent sequences will function in substantially the same manner to produce substantially the same compositions as the nucleic acid and amino acid compositions disclosed and claimed herein. In particular, functionally equivalent DNAs encode proteins that are the same as those disclosed herein or that have conservative amino acid variations, such as substitution of a non-polar residue for another non-polar residue or a charged residue for a similarly charged residue. These changes include those recognized by those of skill in the art as those that do not substantially alter the tertiary structure of the protein.

Two polynucleotides or polypeptides are said to be "identical" if the sequence of nucleotides or amino acid residues in the two sequences is the same when aligned for maximum correspondence. Optimal alignment of sequences for comparison may be conducted by the local homology algorithm of Smith and Waterman, *Adv. Appl. Math.*, 2:482 (1981), by the homology alignment algorithm of Needleman and Wunsch, *J. Mol. Biol.*, 48:443 (1970), by the search for similarity method of Pearson and Lipman, *Proc. Natl. Acad. Sci.* (U.S.A.), 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. These references are incorporated herein by reference.

The percentage of sequence identity between two sequences is determined by comparing two optimally aligned sequences over a window of comparison of at least 20 positions. The percentage is calculated by determining the number of positions at which the identical nucleic acid base or amino acid residue occurs in both sequences to yield the number of matched positions, dividing the number of matched positions by the total number of positions in the window of comparison (i.e., the window size), and multiplying the result by 100 to yield the percentage of sequence identity. A preferred method for comparing sequences uses the GAP program based on the algorithm of Needleman, et at., supra. Typically, the default values for all parameters are selected as follows: gap weight: 5.0, length weight 0.30, average match: 1.0, and average mismatch: 0.0.

As used herein, the phrase "substantial sequence identity" refers to nucleotide or amino acid sequences which share at least 80% sequence identity, preferably 90%, more preferably 95% or more, regardless of the algorithm used to determine sequence identity, compared to a reference sequence over a comparison window of about 20 bp to about 2000 bp, typically about 50 to about 1500 bp, usually about 350 bp to about 1200. The values of percent identity are preferably determined using the GAP program, referred to above. Another indication that nucleotide sequences are substantially identical is if two molecules hybridize to each other under stringent conditions. It is recognized, however, that proteins (and DNA or mRNA encoding such proteins) containing less than the above-described level of homology produced as splice variants or as a result of conservative amino acid substitutions (or substitution of degenerate codons) are contemplated to be within the scope of the present invention.

Alternatively, there are provided polypeptides encoded by nucleic acids that, by virtue of the degeneracy of the genetic code, do not necessarily hybridize to the invention nucleic acids under specified hybridization conditions. Preferred nucleic acids encoding the invention polypeptide are comprised of nucleotides that encode substantially the same amino acid sequence set forth in SEQ ID NO:2. As used herein, the term "degenerate" refers to codons that differ in at least one nucleotide from a reference nucleic acid, e.g., SEQ ID NO:1, but encode the same amino acids as the reference nucleic acid. For example, codons specified by the triplets "UCU", "UCC", "UCA", and "UCG" are degenerate with respect to each other since all four of these codons encode the same amino acid, serine.

Alternatively, preferred nucleic acids encoding the invention polypeptide(s) hybridize under low stringency conditions, preferably moderate stringency conditions to substantially the entire sequence, or substantial portions (i.e., the nucleic acid sequence 1–1440) of the nucleic acid sequence set forth in SEQ ID NO:1.

Stringency of hybridization, as used herein, refers to conditions under which polynucleotide duplex are stable. As known to those of skill in the art, the stability of duplex is a function of sodium ion concentration and temperature (See, for example, Sambrook et al., *Molecular Cloning: A Laboratory Manual* 2d Ed. (Cold Spring Harbor Laboratory, (1989); incorporated herein by reference). Stringency levels used to hybridize a given probe with target-DNA can be readily varied by those of skill in the art.

The phrase "low stringency hybridization" refers to conditions equivalent to hybridization in 10 formamide, 5×Denhart's solution, 6×SSPE, 0.2% SDS at 42C, followed by washing in 1×SSPE, 0.2% SDS, at 50C. Denhart's solution and SSPE (see, e.g., Sambrook et al., *Molecular Cloning, A Laboratory Manual*, Cold Spring Harbor Laboratory Press, 1989) are well known to those of skill in the art as are other suitable hybridization buffers.

As used herein, the phrase "moderately stringent hybridization" refers to conditions that permit target-DNA to bind a complementary nucleic acid that has about 60% identity, preferably about 75% identity, more preferably about 85% identity to the target DNA; with greater than about 90% identity to target-DNA being especially preferred. Preferably, moderately stringent conditions are conditions equivalent to hybridization in 50% formamide, 5×Denhart's solution, 5×SSPE, 0.2% SDS at 42C, followed by washing in 0.2×SSPE, 0.2% SDS, at 65C.

The phrase "high stringency hybridization" refers to conditions that permit hybridization of only those nucleic acid sequences that form stable duplex in 0.018M NaCl at 65C (i.e., if a duplex is not stable in 0.018M NaCl at 65C, it will not be stable under high stringency conditions, as contemplated herein). High stringency conditions can be provided, for example, by hybridization in 50% formamide, 5×Denhart's solution, 5×SSPE, 0.2% SDS at 42C, followed by washing in 0.1×SSPE, and 0.1% SDS at 65C.

In accordance with a still further aspect of the present invention, there are provided complexes comprising the above-described polypeptide, divalent cation metal(s), Tat protein (of functional fragments thereof), and/or protein kinase. Examples of protein kinases include CDK9, functional fragments thereof such as the cyclin T1 binding domain, and the like. As used herein, the term "cyclin T1: Tat complex" refers to a complex comprising cyclin T1, divalent cation metal(s) and Tat (or functional fragments of cyclin T1 and Tat).

In accordance with an alternative aspect of the present invention, there are provided invention complexes which comprise above-described polypeptide and protein kinase which can be dissociated by contacting the complex with a cyclin-dependent kinase inhibitor. Examples of cyclin-dependent kinase inhibitors include flavopiridol, p21, cip1, olomoucine, p27kip1, and the like.

In accordance with still another aspect of the present invention, complexes comprising divalent cation metal and invention peptide and/or protein kinase can be dissociated by contacting the complex with compounds which inhibit the interaction of divalent cation metals with invention polypeptides and/or Tat. In a preferred embodiment of the present invention, there are provided methods for inhibiting the interaction of zinc with invention polypeptides and/or Tat. Removal of zinc destroys the interaction between Tat and cyclin T, while incubation of the proteins with zinc restores the interaction. The divalent cation metals can be readily removed from the Tat-cyclin T complex employing methods known to those of skill in the art. For example, dialysis against buffers containing chelating agents readily exchanges zinc out of the Tat-Cyclin T1 complex, but does not require denaturation of either of the two proteins. Examples of chelating agents include N,N,N',N'-tetrakis(2-pyridylmethyl)ethylenediamine (TPEN), diethyldithiocarbamate (DEDTC) and diphenylthiocarbazone (dithizone), pyrithione, inositol hexakisphosphate, ethylenediamine tetraacetate (EDTA), and the like.

In addition, the interaction between Tat and cyclin T may be blocked by classes of compounds that can reduce individual cysteine residues in multi-zinc complexes, and the like. It has been identified that several of the cysteine residues, especially the cysteine at amino acid residue 261 of SEQ ID NO:2, facilitates binding of cyclin T1 with zinc. Examples of such compounds include inhibitors of the HIV-1 nucleocapsid protein, described in Huang et al., 1998 (J. Med. Chem. 41:1371–1381); McDonnell et al., 1997 (J. Med. Chem. 40:1969–1976); Rice et al., 1993 (Nature 361:473–475); Rice et al., 1995 (Science 270:1194–1197); Rice et al. , 1996 (J. Med. Chem. 39:3606–3616) and Rice et al., 1997 (Nat. Med. 3:341–345), and the like. These compounds (e.g., azodicarbonamide, cystamine, disulfiram, dithiane, and the like) are effective inhibitors of the Tat-human Cyclin T1 interaction in vitro, and thus these compounds and their derivatives may be useful as inhibitors of HIV-1 Tat.

In accordance with another aspect of the present invention, there are provided antibodies having specific reactivity with polypeptides of the present invention, or alternatively CDK9 and/or Tat. Active fragments of antibodies are encompassed within the definition of "antibody". The above-described antibodies can be prepared employing standard techniques, as are well known to those of skill in the art, using, for example, the invention polypeptide or portions thereof as antigens for antibody production (see, e.g., Harlow and Lane, *Antibodies: A Laboratory Manual* (Cold Spring Harbor Laboratory (1988), which is incorporated herein by reference). Preferably, both anti-peptide and anti-fusion protein antibodies can be used (see, for example, Bahouth et al., *Trends Pharmacol. Sci.* 12:338 (1991); Ausubel et al., *Current Protocols in Molecular Biology* (John Wiley and Sons, NY (1989) which are incorporated herein by reference). Factors to consider in selecting portions of invention polypeptide for use as immunogen (as either a synthetic peptide or a recombinantly produced bacterial fusion protein) include antigenicity, accessibility (i.e., where the selected portion is derived from, e.g., the Tat interaction domain, cysteine residues capable of binding divalent cation metals, CDK9 binding domain, and the like), uniqueness of the particular portion selected (relative to known cyclins and kinases), and the like. Altered antibodies such as chimeric, humanized, CDR-grafted or bifunctional antibodies can also be produced by methods well known in the art.

Such antibodies can be employed for studying tissue localization of invention polypeptide, the structure of functional domains, the purification of inhibitors, as well as in diagnostic applications, therapeutic applications, and the like. Preferably, for therapeutic applications, the antibodies employed will be monoclonal antibodies. Invention antibodies can be used to modulate the activity of the polypeptide in living animals, in humans, or in biological tissues or fluids isolated therefrom. Accordingly, there are provided methods of treating a subject infected with HIV, comprising administering to the subject an effective amount of an antibody having specificity for invention polypeptides to block interaction of naturally occurring cyclin T1 to Tat protein. A monoclonal antibody directed to the cysteine residue at amino acid 261, as set forth in SEQ ID NO:2 is especially useful to inhibit interaction of cyclin T1 to divalent cation metal(s).

An example of the means for preparing the invention polypeptide(s) is to express nucleic acids encoding the invention polypeptide in a suitable host cell, such as a bacterial cell , a yeast cell, an amphibian cell (i.e., oocyte), or a mammalian cell, using methods well known in the art, and recovering the expre ssed polypeptide, again using well-known methods. Invention polypeptides can be isolated directly from cells that have been transformed with expression vectors, described below in more detail. The invention polypeptide, biologically active fragments, and functional equivalents thereof can also be produced by chemical synthesis. For example, synthetic polypeptides can be produced using Applied Biosystems, Inc. Model 430A or 431A automatic peptide synthesizer (Foster City, Calif.) employing the chemistry provided by the manufacturer.

Modification of the invention nucleic acids, polypeptides or proteins with the following phrases: "recombinantly expressed/produced", "isolated", or "substantially pure", encompasses nucleic acids, peptides, polypeptides or proteins that have been produced in such form by the hand of man, and are thus separated from their native in vivo cellular environment. As a result of this human intervention, the recombinant nucleic acids, polypeptides and proteins of the invention are useful in ways that the corresponding naturally occurring molecules are not, such as identification of selective drugs or compounds.

The present invention provides isolated nucleic acid encoding cyclin T1 operatively linked to a promoter of RNA transcription, as well as other regulatory sequences. As used herein, the phrase "operatively linked" refers to the functional relationship of the polynucleotide with regulatory and effector sequences of nucleotides, such as promoters, enhancers, transcriptional and translational stop sites, and other signal sequences. For example, operative linkage of a polynucleotide to a promoter refers to the physical and functional relationship between the polynucleotide and the promoter such that transcription of DNA is initiated from the promoter by an RNA polymerase that specifically recognizes and binds to the promoter, and wherein the promoter directs the transcription of RNA from the polynucleotide.

Promoter regions include specific sequences that are sufficient for RNA polymerase recognition, binding and transcription initiation. Additionally, promoter regions include sequences that modulate the recognition, binding and transcription initiation activity of RNA polymerase. Such sequences may be cis acting or may be responsive to trans acting factors. Depending upon the nature of the regulation, promoters may be constitutive, tissue-specific and/or regulated (inducible). Examples of promoters are SP6, T4, L7, T7, SV40 early promoter, metallothionein, cytomegalovirus (CMV) promoter, mouse mammary tumor virus (MMTV) steroid-inducible promoter, Moloney murine leukemia virus (MMLV) promoter, and the like.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression. (See, for example, Kozak, *J. Biol. Chem.* 266:19867 (1991)). Similarly, alternative codons, encoding the same amino acid, can be substituted for coding sequences of the cyclin T1 polypeptide in order to enhance transcription (e.g., the codon preference of the host cell can be adopted, the presence of G-C rich domains can be reduced, and the like).

Also provided are vectors comprising invention nucleic acids. Examples of vectors are viruses, such as baculoviruses and retroviruses, bacteriophages, cosmids, plasmids and other recombination vehicles typically used in the art.

Polynucleotides are inserted into vector genomes using methods well known in the art. For example, insert and vector DNA can be contacted, under suitable conditions, with a restriction enzyme to create complementary ends on each molecule that can pair with each other and be joined together with a ligase. Alternatively, synthetic nucleic acid linkers can be ligated to the termini of restricted polynucleotide. These synthetic linkers contain nucleic acid sequences that correspond to a particular restriction site in the vector DNA.

Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Other means are well known and available in the art.

Further provided are vectors comprising nucleic acids encoding Tat-associating polypeptides, adapted for expression in a bacterial cell, a yeast cell, an amphibian cell (i.e., oocyte), a mammalian cell and other animal cells. The vectors additionally comprise the regulatory elements necessary for expression of the nucleic acid in the bacterial, yeast, amphibian, mammalian or animal cells so located relative to the nucleic acid encoding Tat-associating polypeptide as to permit expression thereof.

As used herein, "expression" refers to the process by which nucleic acids are transcribed into mRNA and translated into peptides, polypeptides, or proteins. If the nucleic acid is derived from genomic DNA, expression may include splicing of the mRNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Sambrook et al. supra). Similarly, a eucaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described above for constructing vectors in general. Expression vectors are useful to produce cells that express the invention polypeptide.

The present invention provides transformed host cells that recombinantly express invention polypeptides. An example of a transformed host cell is a mammalian cell comprising a plasmid adapted for expression in a mammalian cell. The plasmid contains nucleic acid encoding an invention polypeptide and the regulatory elements necessary for expression of invention proteins. Various mammalian cells may be utilized as hosts, including, for example, mouse fibroblast cell NIH3T3, CHO cells, HeLa cells, Ltk-cells, etc. Expression plasmids such as those described supra can be used to transfect mammalian cells by methods well known in the art such as, for example, calcium phosphate precipitation, DEAE-dextran, electroporation, microinjection or lipofection.

The present invention provides nucleic acid probes comprising nucleotide sequences capable of specifically hybridizing with sequences included within nucleic acids encoding invention polypeptides, for example, a coding sequence included within the nucleotide sequence shown in SEQ ID NO:1. As used herein, a "probe" is a single-stranded DNA or RNA that has a sequence of nucleotides that includes at least 15 contiguous bases, preferably at least 20, more preferably at least 50, contiguous bases that are the same as (or the complement of) any 15 or more contiguous bases set forth in any of SEQ ID NO:1. Preferred regions from which to construct probes include 5' and/or 3' coding sequences, sequences within the open reading frame (ORF), and the like. Full-length or fragments of cDNA clones encoding cyclin T1 can also be used as probes for the detection and isolation of related genes. When fragments are used as probes, preferably the cDNA sequences will be from the carboxyl end-encoding portion of the cDNA, and most preferably will include cysteine residues capable of associating with divalent cation metal(s)/Tat.

As used herein, the terms "label" in its various grammatical forms refer to substituents such as single atoms and molecules that are either directly or indirectly involved in the production of a readily detectable signal. Any label can be linked to invention nucleic acid probes, expressed proteins, polypeptide fragments, or antibody molecules. These atoms or molecules can be used alone or in conjunction with additional reagents. Such labels are themselves well-known in clinical diagnostic chemistry. Examples of readily detectable substituents include radiolabeled molecules, fluorescent molecules, enzymes (such as glutathione-S-transferase (GST), histidine (his) and the like), specific-binding ligands, and the like.

As used herein, the phrase "specifically hybridizing" encompasses the ability of a polynucleotide to recognize a sequence of nucleic acids that are complementary thereto and to form double-helical segments via hydrogen bonding between complementary base pairs. Nucleic acid probe technology is well known to those skilled in the art who will readily appreciate that such probes may vary greatly in length and may be labeled with a detectable agent, such as a radioisotope, a fluorescent dye, and the like, to facilitate detection of the probe. Invention probes are useful to detect the presence of nucleic acids encoding the cyclin T1 polypeptide. For example, the probes can be used for in situ hybridizations in order to locate biological tissues in which the invention gene is expressed. Additionally, synthesized oligonucleotides complementary to the nucleic acids of a nucleotide sequence encoding cyclin T1 polypeptide are useful as probes for detecting the invention genes, their associated mRNA, or for the isolation of related genes using homology screening of genomic or cDNA libraries, or by using amplification techniques well known to one of skill in the art.

As used herein, "transgenic animal" refers to an animal that contains an inheritable recombinant transgene. In accordance with the present invention, any animal species can be rendered transgenic by introduction of nucleic acids encoding invention polypeptides. Also provided are transgenic animals capable of expressing nucleic acids encoding complexes comprising invention polypeptides and protein kinases such as CDK9. The present invention also provides transgenic animals having a genome comprising antisense nucleic acids complementary to nucleic acids encoding invention polypeptides placed so as to be transcribed into antisense mRNA complementary to mRNA encoding invention polypeptides, which hybridizes thereto and, thereby, reduces the translation thereof. The nucleic acid may additionally comprise an inducible promoter and/or tissue specific regulatory elements, so that expression can be induced, or restricted to specific cell types. Examples of nucleic acids are DNA or cDNA having a coding sequence substantially the same as the coding sequence shown in SEQ ID NO:1. As employed herein, "animals" embraces mammals and non-mammals, including human, rodent, primate, avian, bovine, porcine, ovine, canine, feline, amphibian, reptile, and the like.

Animal model systems which elucidate the physiological and behavioral roles of HIV infection are produced by creating transgenic animals in which Tat transactivation is induced. Examples of such techniques include the insertion of normal or mutant versions of nucleic acids encoding a cyclin T1 polypeptide, optionally in the presence of CDK9 polypeptide, by microinjection, retroviral infection or other means well known to those skilled in the art, into appropriate fertilized embryos to produce a transgenic animal, and then introducing HIV, or the Tat protein, to the mature animal. (See, for example, Hogan et al., *Manipulating the Mouse Embryo: A Laboratory Manual* (Cold Spring Harbor Laboratory, (1986)). Alternatively, the cyclin T1 counterpart in the animal, such as in rodents, can be mutated to induce Tat transactivation by inducing assocation of Tat with divalent cation metals(s), i.e., inserting cysteine residues in the cyclin T1 counterpart to induce formation of a cyclin:divalent cation metal(s):Tat complex.

In contrast to homologous recombination, microinjection adds genes to the host genome, without removing host genes. Microinjection can produce a transgenic animal that is capable of expressing endogenous cyclin T1 protein. Inducible promoters can be linked to the coding region of nucleic acids to provide a means to regulate expression of the transgene. Tissue specific regulatory elements can be linked to the coding region to permit tissue-specific expression of the transgene. Transgenic animal model systems are useful for in vivo screening of compounds for identification of specific antagonists which inhibit Tat transactivation.

Invention nucleic acids, oligonucleotides (including antisense), vectors containing same, transformed host cells, polypeptides and combinations thereof, as well as antibodies of the present invention, can be used to screen compounds in vitro to determine whether a compound functions as a potential antagonist to invention polypeptides. These in vitro screening assays provide information regarding the function and activity of invention polypeptides, which can lead to the identification and design of compounds that are capable of specific interaction with one or more types of polypeptides, peptides or proteins.

In accordance with still another embodiment of the present invention, there are provided methods for identifying compounds which bind invention polypeptides. The invention proteins may be employed in a competitive binding assay. Such an assay can accommodate the rapid screening of a large number of compounds to determine which compounds, if any, are capable of binding invention proteins. Subsequently, more detailed assays can be carried out with those compounds found to bind invention proteins, to further determine whether such compounds act as modulators, agonists or antagonists of invention polypeptides.

In accordance with still another embodiment of the present invention, there are provided methods to identify compounds which disrupt the association of divalent cation metal(s) with cyclin T1 and/or Tat protein, said methods comprising:

(a) contacting a complex with a test compound, said complex comprising divalent cation metal(s) with cyclin T1 and/or Tat protein, (b) monitoring for the presence of divalent cation metal(s) independent of cyclin T1 and/or Tat protein, and (c) identifying those compounds which induce release of divalent cation metal(s) as compounds which disrupt the association of divalent cation metal(s) complex with cyclin T1 and/or Tat protein.

In accordance with still another embodiment of the present invention, there are provided methods to identify compounds which disrupt complex comprising Tat protein, divalent cation metal(s) and cyclin T1; said methods comprising:

(a) contacting a host cell with a test compound,
wherein said host cell comprises:
a first fusion protein comprising a GAL4 DNA binding domain (or, in an alternative embodiment, an activation domain), operatively associated with Tat-1,
a second fusion protein comprising an activation domain (or, in an alternative embodiment, a GAL4 DNA binding domain), operatively associated with the Tat binding region of cyclin T1,
divalent cation metal(s), and
a reporter construct comprising a GAL4 response element operatively linked to a reporter gene; and (b) selecting those test compounds which cause reduced expression of the reporter gene product as compounds which disrupt complex comprising Tat protein, divalent cation metal(s) and cyclin T1.

As readily recognized by those of skill in the art, the above-described assay can be modified to facilitate identification of compounds which disrupt any of the specific interactions involved in the formation of the above-described complex. For example, those of skill in the art recognize that the entire Tat protein and cyclin T1 polypeptide can be employed in the above-described assay.

In accordance with still another embodiment of the present invention, there are provided methods to identify compounds which disrupt complex comprising compounds which disrupt complex comprising CDK9 and cyclin T1, said methods comprising:

(a) contacting a host cell with a test compound,
wherein said host cell comprises:
a first fusion protein comprising a GAL4 DNA binding domain (or, in an alternative embodiment, an activation domain), operatively associated with CDK9,
a second fusion protein comprising an activation domain (or, in an alternative embodiment, a GAL4 DNA binding domain), operatively associated with cyclin T1, and
a reporter construct comprising a GAL4 response element operatively linked to a reporter gene; and (b) selecting those test compounds which cause reduced expression of the reporter gene product as compounds which disrupt complex comprising CDK9 and cyclin T1.

As readily recognized by those of skill in the art, the above-described assay can be modified to facilitate identification of compounds which disrupt any of the specific interactions involved in the formation of the above-described complex. For example, those of skill in the art recognize that the individual domains, of CDK9 and cyclin T1, which interact with the corresponding domains, of cyclin T1 and CDK9, respectively, can be employed in the above-described assay.

As used herein, the term "disrupt" embraces compounds which cause substantially complete dissociation of the various components of the complex, as well as compounds which merely alter the conformation of one or more components of the complex so as to reduce the repression otherwise caused thereby.

As readily understood by those of skill in the art, a wide variety of compounds can be assayed employing the invention method. Any compound with the potential to act as a compound which disrupts cyclin T1 complexes can be tested, e.g., steroid or steroid-like compounds, pharmaceutically active compounds, naturally occurring compounds, synthetic organic compounds, and the like.

Any cell line can be used as a suitable "host" for the functional bioassay contemplated for use in the practice of the present invention. Thus, cells contemplated for use in the practice of the present invention include transformed cells, non-transformed cells, neoplastic cells, primary cultures of different cell types, and the like. Exemplary cells which can be employed in the practice of the present invention include Schneider cells, CV-1 cells, HuTu80 cells, F9 cells, NTERA2 cells, NB4 cells, HL-60 cells, 293 cells, Hela cells, yeast cells, and the like. Preferred host cells for use in the functional bioassay system are COS cells and CV-1 cells. COS-1 (referred to as COS) cells are monkey kidney cells that express SV40 T antigen (Tag); while CV-1 cells do not express SV40 Tag. The presence of Tag in the COS-1 derivative lines allows the introduced expression plasmid to replicate and provides a relative increase in the amount of receptor produced during the assay period. CV-1 cells are presently preferred because they are particularly convenient for gene transfer studies and provide a sensitive and well-described host cell system.

The above-described cells (or fractions thereof) are maintained under physiological conditions when contacted with physiologically active compound. "Physiological conditions" are readily understood by those of skill in the art to comprise an isotonic, aqueous nutrient medium at a temperature of about 37C.

Various constructs employed in the practice of the present invention are well known in the art. Thus, the GAL4 DNA binding domain, the activation domain, GAL4 response elements and various members of the basal transcription machinery have all been well characterized and extensively discussed in the art. For example, the DNA binding domain of the yeast GAL4 protein comprises at least the first 74 amino acids thereof (see, for example, Keegan et al., *Science* 231: 699–704 (1986)). Preferably, the first 90 or more amino acids of the GAL4 protein will be used, with the first 147 amino acid residues of yeast GAL4 being presently most preferred.

Activation domains contemplated for use in the practice of the present invention are well known in the art and can readily be identified by the artisan. Examples include GAL4 activation domain, BP64, VP16, and the like.

Exemplary GAL4 response elements are those containing the palindromic 17-mer:

5'-CGGAGGACTGTCCTCCG-3' (SEQ ID NO:3), such as, for example, 17MX, as described by Webster et al., in Cell 52: 169–178 (1988), as well as derivatives thereof. Additional examples of suitable response elements include those described by Hollenberg and Evans in *Cell* 55:899–906 (1988); or Webster et al. in *Cell* 54:199–207 (1988).

Reporter constructs contemplated for use in the practice of the present invention comprise:

(a) a promoter that is operable in the host cell,
(b) a response element, and
(c) a reporter gene,
wherein the reporter gene is operatively linked to the promoter for transcription of the reporter gene, and
wherein the response element is operatively linked to the promoter for activation thereof.

Exemplary reporter genes include chloramphenicol transferase (CAT), luciferase (LUC), beta-galactosidase (β-gal), and the like. Exemplary promoters include the simian virus (SV) promoter or modified form thereof (e.g., DSV), the thymidine kinase (TK) promoter, the mammary tumor virus (MTV) promoter or modified form thereof (e.g., DMTV), and the like [see, for example, Mangelsdorf et al., in Nature 345:224–229 (1990), Mangelsdorf et al., in Cell 66:555–561 (1991), and Berger et al., in J. Steroid Biochem. Molec. Biol. 41:733–738 (1992)].

As used herein, the phrase "operatively associated with" means that the respective DNA sequences (represented, for example, by the terms "GAL4 response element" and "reporter gene") are operational, i.e., work for their intended purposes; the word "functionally" means that after the two segments are linked, i.e., upon appropriate activation by a cyclin T1:Tat complex or cyclin T1:CDK9 complex, the reporter gene will be expressed as the result of the fact that the corresponding "response element" was "turned on" or otherwise activated.

In accordance with still another embodiment of the present invention, there are provided methods to identify compounds which block the interaction of the cyclin T1:Tat complex with TAR RNA, said method comprising:

(a) contacting a host cell with a test compound, and
(b) selecting those test compounds which cause reduced expression of the reporter nucleic acid product as compounds which block the interaction of the cyclin T1:Tat complex with TAR RNA;
wherein said host cell comprises a Tat protein, divalent cation metal(s), cyclin T1, CDK9 and a reporter construct comprising a TAR RNA operatively linked to nucleic acid encoding a reporter protein. According to this method, complex comprising cyclin T1, divalent cation metal(s) and Tat protein are contacted with an "unknown" or test substance (in the presence of a TAR RNA operatively associated with a reporter gene construct when antagonist activity is tested), the activity of reporter gene is monitored subsequent to the contact with the "unknown" or test substance, and those substances which cause the reduced expression of the reporter gene construct are identified as compounds which block the interaction of the cyclin T1:Tat complex with TAR RNA.

In accordance with still another embodiment of the present invention, there are provided methods to identify compounds which disrupt complex comprising Tat protein, divalent cation metal(s) and cyclin T1, said method comprising:

(a) contacting an affinity matrix with a test compound, wherein the affinity matrix comprises an affinity support, Tat protein, divalent cation metal(s), and cyclin T1; and
(b) selecting those test compounds which cause the release of Tat, divalent cation metal(s) and/or cyclin T1 from said support as compounds which disrupt complex comprising Tat protein, divalent cation metal(s) and cyclin T1.

As readily recognized by those of skill in the art, the above-described assay can be modified, wherein either Tat protein or cyclin T1 is operatively associated with a label. Examples of preferred labels include glutathione-S-methionine (GST) or histidine (HIS).

In accordance with yet another embodiment of the present invention, there are provided methods to identify compounds which disrupt the interaction of the cyclin T1:Tat complex with TAR RNA, said method comprising:

(a) contacting an affinity matrix with a test compound, (b) selecting those test compounds which cause the release of TAR RNA from said support as compounds which disrupt the interaction of the cyclin T1:Tat complex with TAR RNA;

wherein the affinity matrix comprises an affinity support, a cyclin T1, divalent cation metal(s), a Tat protein, and a TAR RNA.

As readily recognized by those of skill in the art, the above-described assays can be modified to facilitate identification of compounds which disrupt any of the specific interactions involved in the formation of the above-described complex.

In accordance with still another embodiment of the present invention, there are provided methods for the modulation of Tat transactivation in a biological system, the method comprising contacting the system with an effective amount of a compound identified by the above-described methods, thereby modulating said Tat transactivation.

In accordance with y et another embodiment of the present invention, there are provided methods to treat a subject infected with HIV, such methods comprising administering to the subject an effective amount of compounds which mimics and/or masks invention polypeptides. An example of compounds which would mimic the invention polypeptide include polypeptides which bind Tat protein but are unable to enhance the affinity of Tat for TAR RNA, and the like. Examples of such compounds include cyclin T1 fragments encoded by nucleic acids which hybridize, under low stringency conditions, to nucleotide sequence 1–380 set forth in SEQ ID NO:1. Examples of compounds which mask invention polypepetides include compounds which bind cyclin T1, such as Tat-1, Tat-2 and the like.

In accordance with a still further embodiment of the present invention, there are provided methods for modulating Tat transactivation, said methods comprising contacting a biological system with an effective amount of a compound which inhibits the cyclin T1:Tat complex and/or cyclin T1:Tat:TAR RNA complex. Such compounds inhibit Tat activity in HIV infected cells by preventing the interaction of Tat with the cyclin T1 protein and/or block the binding of the cyclin T1:Tat complex to TAR RNA. Compounds which specifically mask or mimic these associations have fewer undesired side effects on the expression of host cell genes than do existing drugs used to inhibit the relatively weak association of Tat with the bulge of TAR RNA (Hamy et al. (1997) *Proc Natl Acad Sci USA* 94:3548–3553) or that target the active site of the CDK9 kinase (Mancebo et al. (1997) *Genes & Dev* 11:2633–2644).

As employed herein, the term "modulate" refers to the ability of a polypeptide to directly (by binding to Tat) induce expression of gene(s) maintained under Tat expression control, or to repress expression of gene(s) maintained under such control.

As employed herein, the phrase "Tat transactivation" refers to activation of viral gene expression by synthesis of proviral RNA transcripts encoding viral structural proteins. Modulation of such processes can be accomplished in vitro or in vivo. In vivo modulation can be carried out in a wide range of subjects, such as, for example, humans, rodents, sheep, pigs, cows, and the like.

As employed herein, the phrase "biological system" refers to an intact organism or a cell-based system containing the various components required for response to the compounds described herein, e.g., cyclin T1, optionally in the presence of CDK9, Tat, and an Tat-responsive reporter (which typically comprises a transactivation response element (TAR) in operative communication with a reporter gene; suitable reporters include luciferase, chloramphenicol transferase, β-galactosidase, and the like.

Contacting in a biological system contemplated by the present invention can be accomplished in a variety of ways, and the treating agents contemplated for use herein can be administered in a variety of forms (e.g., in combination with a pharmaceutically acceptable carrier therefor) and by a variety of modes of delivery. Exemplary pharmaceutically acceptable carriers include carriers suitable for oral, intravenous, subcutaneous, intramuscular, intracutaneous, and the like administration. Administration in the form of creams, lotions, tablets, dispersible powders, granules, syrups, elixirs, sterile aqueous or non-aqueous solutions, suspensions or emulsions, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use.

As employed herein, the phrase "effective amount" refers to levels of compound sufficient to provide circulating concentrations high enough to modulate the expression of gene(s) mediated by members of the steroid/thyroid superfamily of receptors. Such a concentration typically falls in the range of about 10 nM up to 2 mM; with concentrations in the range of about 100 nM up to 500 nM being preferred. Since the activity of different compounds described herein may vary considerably, and since individual subjects may present a wide variation in severity of symptoms, it is up to the practitioner to determine a subject's response to treatment and vary the dosages accordingly.

Figure 2:
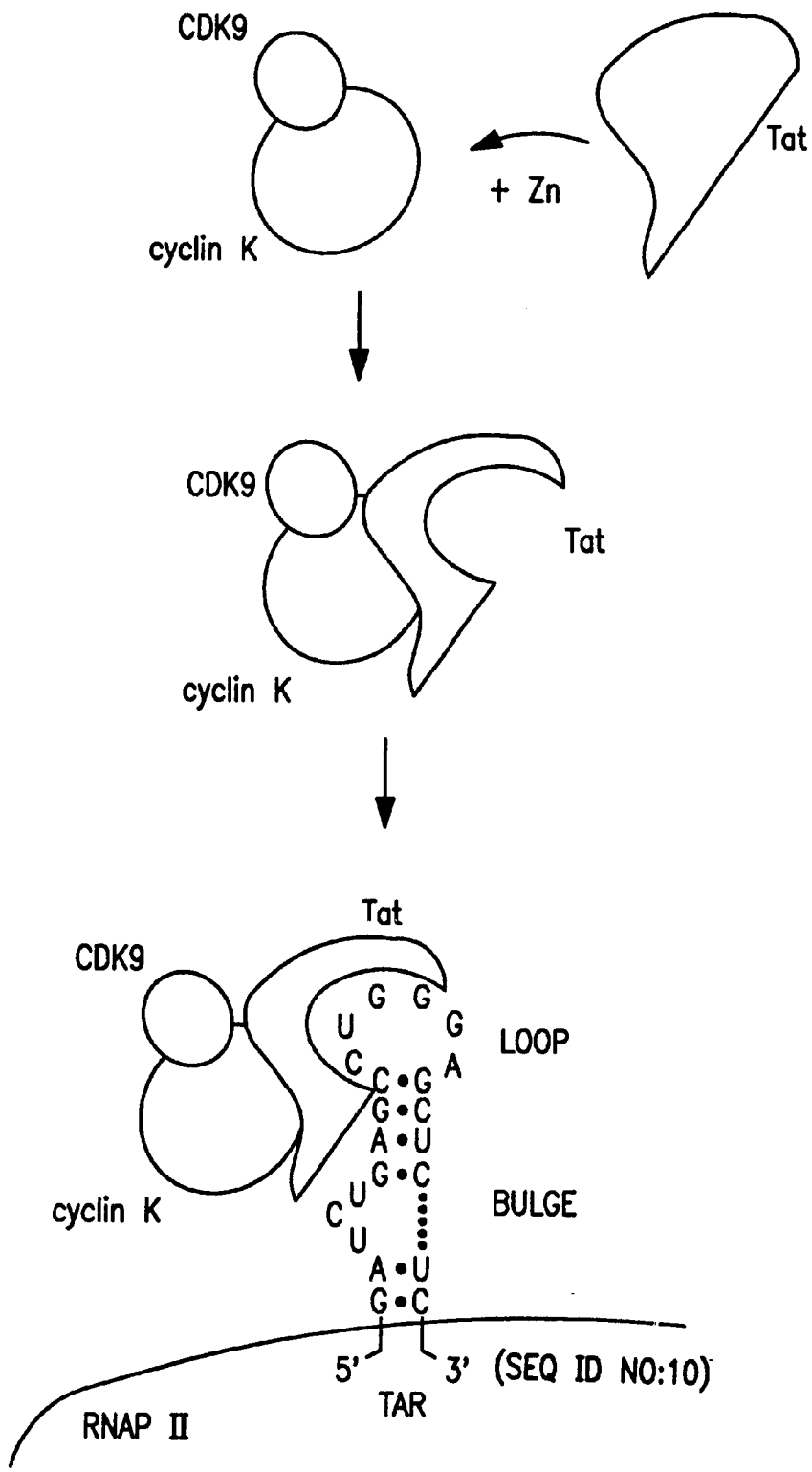
FIG. 2 provides a biochemical view of the interaction of Tat with cyclin T1, and the subsequent co-operative binding of Tat and the TAK/P-TEFb complex to TAR RNA (SEQ ID NO:10).

In summary, a novel 87 kDa cyclin C-related protein (called cyclin T1) has been identified as the host cell factor that interacts with the human immunodeficiency virus (HIV) Tat protein, presumably through divalent cation metals. Cyclin T1 is a partner for CDK9 (PITALRE), a CDC2-related kinase that has been shown previously to hyperphosphorylate the RNAPII carboxyl-terminal domain as an essential subunit of the positive-acting transcription elongation factor complex, P-TEFb (Mancebo et al. (1997) *Genes Dev* 11:26332–2644). Yang et al. (1997) *Proc Natl Acad Sci USA* 94:12331–12336; Zhu et al. (1997) *Genes Dev* 11:2622–2632). It is shown herein that Tat and cyclin T1 bind in a highly co-operative manner to TAR RNA in vitro. Moreover, the cyclin T1-Tat complex, unlike free Tat, is able to discriminate effectively between wild-type and loop mutant TAR RNAs, and thus the binding of the cyclin T1-Tat complex to wild-type and mutant TAR RNAs correlates precisely with the ability of the various TAR elements to support Tat transactivation. Although it has been generally assumed that the transcriptional coactivator for Tat would be distinct from its TAR RNA-binding cofactor, these findings reveal that a single molecule (cyclin T1) subserves both functions (FIG. 2). Through this mechanism, the cyclin T1-Tat complex provides a direct link between CDK9 and nascent TAR RNA transcripts on the paused RNA polymerase II complex. Co-operative binding to TAR RNA would serve to ensure that TAR molecules are bound only by Tat proteins that have previously associated with cyclin T1-CDK9 complexes in the cell. The cyclin T1 protein has no intrinsic affinity for RNA, and that its association with TAR depends entirely upon both the activation domain and the ARM of Tat. Consequently, these findings suggest that Tat acts to target cyclin T1-CDK9 complexes to nascent viral RNA transcripts in order to increase the number of RNAPII complexes that are competent for transcription elongation.

The invention will now be described in greater detail by reference to the following non-limiting examples.

EXAMPLE 1

In vitro Comparison of the Relative Abilities of the HIV-1 and HIV-2 TAR RNAs to Inhibit Tat Activation in Trans Although the interaction between the HIV-1 Tat protein and its cognate TAR RNA has been studied extensively, relatively little is known about the sequence requirements for binding of Tat to the TAR RNA of HIV-2, which contains a duplicated hairpin structure with loop and bulge sequences that are nearly identical to those found in TAR-1 RNA (see below). To compare the properties of the HIV-1 and HIV-2 TAR RNAs, in vitro transcription reactions were carried out to assess the relative transcriptional activity of the HIV-1 and HIV-2 promoters, as well as the ability of exogenous (SP6-transcribed) TAR-1 and TAR-2 RNAs to inhibit transactivation by the HIV-1 and HIV-2 Tat proteins.

The Tat proteins of HIV-1 and HIV-2 strongly activate transcription from the HIV-2 promoter (45- to 50-fold) whereas the HIV-1 promoter is induced strongly by HIV-1 Tat but only weakly (5.4-fold) by the HIV-2 Tat. Bacterial expression vectors for the following glutathione S-transferase (GST) Tat fusions were obtained from Dr. Andrew Rice through the AIDS Research and Reference Program, NIH: Tat-1 86 (two exon), Tat-2 (aa1–99; single exon), Tat-2 (aa1–99; Δ8–47), Tat-2 (aa1–130; two exon) and Tat-1 (aa1–48). Tat-1 (aa1–86; Δ1–47), Tat-2 (aa1–99; Δ1–64) Tat-2 (aa1–99; Δ1–77), and Tat-2 (aa1–130; Δ1–77) were cloned by standard PCR procedures into the BamHI/EcoRI sites within pGEX-2T. For all clones, the parent vectors Tat-1 86 (HXB2 isolate) and Tat-2 (aa1–130; Rod isolate) were used as templates. All GST Tat fusions were expressed and purified as described (Rhim et al. (1994) *J. Acquir. Immune. Defic. Syndr.* 7:1116–1121). Tat does not stimulate transcription from an HIV-2 template that lacks TAR (DT), indicating that transactivation is specific under these conditions, and high levels of these full-length Tat proteins did not inhibit ("squelch") HIV transcription, as has been observed with truncated Tat proteins that lack the Tat ARM and C-terminal domain. The relative inability of Tat-2 to activate transcription from the HIV-1 promoter is consistent with previous in vivo results from transient expression assays, and has been attributed to differences in the ARM regions of the two Tat proteins that influences the ability of Tat-2 to recognize TAR-1 RNA.

To assess the ability of exogenous HIV-1 and HIV-2 TAR RNAs to inhibit Tat activation, wild-type and loop or bulge mutant versions of the two TAR RNAs were expressed and examined for their relative ability to compete for Tat transactivation in vitro. The plasmids pH96 WT and pH 96 30/33 contain a single copy of TAR-1 cloned into pGEM-1 (Sheline et al. (1991) *Genes Dev* 5:2508–2520). The single wild-type loop sequence C<u>UGGG</u> within pH96 30/33 was also changed to C<u>GUUU</u>. pH96 was linearized with Hind III and transcribed with T7 RNA polymerase. The plasmid DNAs used for the in vitro synthesis of the wild-type and bulge deletion TAR-2 RNAs (UU:Δ, the 3' bulge deletion; Δ:UA, the 5' bulge deletion; and Δ:Δ, the double bulge deletion) were obtained from Dr. Andrew Rice (Baylor Univ.) and have been described previously (Rhim et al. (1994) *J Acquir Immune Defic Syndr* 7:1116–1121; Rhim. and Rice (1994) *Virol.* 202:202–211). Plasmid DNAs for these TAR RNAs were linearized with Hind III and transcribed with T7 RNA polymerase. TAR-2 Wt DNA was linearized with EcoRI and transcribed with Sp6 RNA polymerase for use as TAR-2 antisense (AS) RNA. pTAR-2 poly A WT and pTAR-2 poly A LM, the double loop mutant, was cloned by PCR and inserted into the Hind III/BamHI sites within the pSP64 poly A vector (Promega). The two wild-type loop sequences C<u>UGGG</u> were changed to C<u>GUUU</u>. pTAR-2 poly A was linearized with BamHI and transcribed with Sp6 RNA polymerase. Similar to TAR-2 Wt above, pTAR-2 poly A contains the full HIV2 TAR element (+1 to +123) from HIV2 Rod.

The wild-type TAR-1 and TAR-2 RNAs are both observed to be effective competitors for Tat transactivation, although the TAR-2 RNA is approximately four-fold more effective than TAR-1 as an inhibitor of HIV-2 transcription, and point mutations affecting four residues of the pentanucleotide loop of either TAR RNA eliminate its ability to inhibit Tat activation. Therefore, the specific inhibition of Tat transactivation by exogenous TAR-1 or TAR-2 decoy RNAs requires sequences in the apical loop of the RNA hairpin structure.

EXAMPLE 2

Optimal Binding of HIV-1 and HIV-2 Tat Proteins to TAR-2 RNA Requires Sequences in the Loop of TAR To determine the extent to which binding of the HIV-1 and HIV-2 Tat proteins to TAR RNA might correlate with TAR function, the ability of the purified full-length Tat-1 and Tat-2 proteins to bind to the same HIV TAR RNAs that had been tested for inhibition of Tat transactivation in vitro was assessed. Large scale TAR synthesis was performed in a 0.4 ml reaction volume at 37C for 2 hours and contained 40 mM Tris (pH 8.0), 2 mM spermidine, 20 mM DTT, 6 mM $MgCl_2$, 0.5 mM in each ribonucleotide triphosphate, 20 pmole linear DNA template, 0.8 units/ml T7/Sp6 RNA polymerase (Ambion), and 100 units RNasin (USB). Small scale, high specific activity TAR synthesis was carried out under similar conditions except that the volume was 0.08 ml, incubation time was one hour, linear DNA template was one pmole, $^{32}$P-UTP (30 uCi, 800 Ci/mmol, 20 uCi/ul, Amersham) was included while cold UTP was reduced to 20 uM.

After digestion of the DNA template with 2 units DNase 1 (Promega) per μg DNA, reaction mixtures were extracted once with phenol:chloroform, once with chloroform, ammonium acetate added to 2.5 M and precipitated with 2.5 volumes ethanol. The RNA pellet was dissolved in 0.1 M NaCl and applied to a G-50 spin column (Boehringer). RNA was quantitated by OD at 260 nm (large scale) and/or by radioactive incorporation (small scale). TAR RNA used for the gel shift probe was heated to 88C in the presence of 1 mM $MgCl_2$ and cooled to room temperature over 15 minutes.

Gel mobility shift experiments indicate that the HIV-1 and HIV-2 Tat proteins bind much more avidly to TAR-2 RNA than to TAR-1 RNA in vitro. The HIV-1 Tat protein binds considerably more strongly to its cognate TAR-1 RNA than does the HIV-2 Tat protein, which is consistent with previous findings from other groups, and has been attributed to difference in the arginine-rich motifs of the two Tat proteins. As a result, the discrimination between TAR-2 and TAR-1 RNAs is most pronounced for the HIV-2 Tat protein. Both Tat proteins form several specific complexes with TAR-2 RNA, and do not bind either anti-sense TAR transcripts (AS) or TAR-2 RNAs carrying a deletion of the bulge region in both of the upper hairpin stems (Dbb-2).

Interestingly, binding of either Tat protein is dramatically reduced by a four base substitution of residues in the pentanucleotide loop in each of the TAR-2 stem-loop structures. The comparable loop substitution mutation only modestly reduces binding of the HIV-1 Tat to TAR. Although these results were obtained with GST-Tat fusion proteins, identical results are obtained with Tat proteins lacking the GST moiety and competition experiments indicate that the binding of Tat-2 to wild-type TAR-2 RNA occurs with at least a ten-fold higher affinity than the binding to the loop mutant version of TAR-2.

These data indicate that the full-length Tat proteins is capable of discriminating between wild-type and loop mutant TAR RNAs, although the effect is more dramatic on TAR-2 and on TAR-1. Moreover, Tat binds much more strongly to both the wild-type and loop mutant TAR-2 RNA than to the wild-type TAR-1 RNA, which provides further evidence that the binding of native Tat to TAR in vitro does not correlate with the role of TAR in Tat transactivation.

EXAMPLE 3

The Amino Terminal Region of Tat Negatively Regulates TAR RNA-binding Affinity and Is Required for Efficient Loop-specific Binding to TAR-2

It has been reported previously by others that the TAR-1 and TAR-2 RNAs are recognized in a nearly equivalent manner by Tat in vitro. Removal of amino terminal residues (aa8–47) of Tat-2 greatly enhances the Tat:TAR interaction, indicating that sequences at the amino terminus of the intact Tat protein negatively regulate TAR RNA-binding activity. Tat proteins containing more extensive truncations that remove the Cys-rich region (aa1–64, aa1–70) bind TAR RNA even more efficiently. Equivalent results are obtained with either the one-exon (aa1–99) or two-exon (aa1–130) Tat-2 protein, and comparable truncations of Tat-1 have the same effect on TAR RNA-binding activity.

It was next examined whether the RNA-binding specificity of Tat-2 is altered upon loss of the transactivation domain. To compare directly the RNA-binding properties of the wild-type and truncated Tat proteins, the full-length Tat-1 or Tat-2 proteins were analyzed at six-fold higher levels than the truncated Tat proteins in gel mobility shift experiments carried out with various TAR-1 and TAR-2 RNAs. Although the RNA-binding specificity of the full-length and truncated Tat proteins could be compared directly under these conditions, the truncated Tat proteins have higher overall RNA-binding activity at these concentrations. Interestingly, mutations that affect the loop of TAR-2 RNA have a much more deleterious effect on the binding of the full-length Tat proteins than on the binding of the truncated Tat proteins. The truncated Tat-1 protein displays an approximately four-fold higher affinity for TAR-2 than TAR-1. By contrast, the full-length Tat-1 protein binds much more avidly to TAR-1 than to TAR-2. Similarly, deletions that remove either the 5' or 3' bulge in the TAR-2 RNA structure have a more dramatic effect on the binding of the full-length Tat than truncated Tat proteins. These findings indicate that the amino terminal region of Tat contributes significantly to the specificity of the Tat:TAR interaction.

The truncated Tat proteins were found to form a second complex with wild-type TAR-2 RNA, which is not observed with TAR-2 loop mutant RNA. At high ratios of mutant Tat protein to RNA, nearly equivalent amounts of the C1 and C2 complex form. To better characterize these different Tat:RNA complexes, the residues in TAR that are directly contacted by Tat were analyzed by an ethylation-interference footprint technique. Wild-type TAR-2 RNA was subjected to ethylation and two different Tat:TAR-2 complexes (designated C2 and FL) were excised from the gel and analyzed. Interestingly, the loop-sensitive complex formed efficiently with the full-length Tat-2 protein (FL) and inefficiently by the truncated Tat-2 protein (C2) generated identical patterns of RNA footprint protection. T4 RNA ligase and [5'-$^{32}$P]pCp was used to label TAR-2 RNA at the 3' end as described previously (Churcher et al. (1993) *J Mol Biol* 230:90–110). A 20 ml reaction contained 50 mM Tris pH 8.0, 3 mM DTT, 10 mM $MgCl_2$, 25 mM NaCl, 50 mM ATP, 200 pmoL RNA transcribed from pTAR-2 poly A, 65 mCi [$^{32}$P]pCp (3000 Ci/mmole, Andotek), 40 units T4 RNA ligase (NEB), 80 units RNasin (USB), 25 mg/ml BSA, and 10% DMSO.

Following an overnight incubation at 4C, the RNA was extracted with phenol/chloroform, precipitated once with ammonium acetate and passed through a G-50 spin column to remove residual free label. Typical yield was 2.5×10$^4$ cpm/pmole RNA. Dephosphorylated TAR-2 RNA was labeled at the 5' end in a reaction containing 70 mM Tris pH 7.6, 10 mM $MgCl_2$, 5 mM DTT, 20 mM NaCl, 100 pmole (5 mg) TAR RNA, 100 uCi [g-$^{32}$P]ATP (6000 Ci/mmole, ICN), and 10 units T4 polynucleotide kinase (NEB). Typical yield was 1×10$^5$ cpm/pmole RNA. DEPC modification of TAR RNA was carried out using 2 mg of 5'- or 3'-end labeled TAR RNA, 1 ml DEPC and a seven minute incubation at 90C. The RNA was immediately chilled on ice, applied to a G-50 spin column and precipitated with ethanol. The pellet was resuspended in 0.1 M NaCl and 1 mM $MgCl_2$, heated to 70C and slowly refolded.

Labelled and modified TAR RNA was bound to either GST-Tat-2 (99) WT or GST-Tat-2 (99) D1-77 and the complex was purified on a nondenaturing polyacrylamide gel using the gel shift conditions stated above with the following modifications per reaction: an increase to 25 ng TAR and either 500 ng of the WT or truncated GST-Tat-2 proteins. The gel was exposed to film and the desired bands were excised from the gel and eluted overnight in 2 ml of an RNA elution buffer (0.5 M ammonium acetate, 0.1% SDS) The mixture was extracted with phenol/chloroform, precipitated with ethanol without additional salt, and the pellet was washed with 80% ethanol. Cleavage of modified TAR RNA with aniline was as described (Conway and Wickens (1987)

EMBO J. 6:4177–4184) and the RNA footprints were analyzed on a 12% denaturing polyacrylamide sequencing gel. For RNase T1 digestion of TAR RNA, reactions were prepared with 5 mg tRNA, 25 ng TAR RNA, and 1 ml of a 1:60 dilution of RNase T1 (Boehringer, 100 units/ul) in the standard 16 ml RNA-binding reaction described above. Following a 30 min. incubation on ice, the RNA was extracted with phenol, precipitated with ethanol, and resuspended in formamide loading buffer.

Ethylation of residues in the bulge and surrounding stem of each of the two TAR-2 stem-loop structures is seen to be sufficient to prevent binding of Tat to TAR-2 RNA, indicating that Tat makes direct contacts with both of the upper stems of TAR-2. The binding site for Tat on the 3' stem is more extensive than that observed on the 5' stem, which could reflect multiple sites for Tat interaction or differences in the conformation of the RNA between the two hairpin structures.

By contrast with the loop-sensitive Tat:TAR-2 complexes, the loop-insensitive C1 complex that was preferentially formed with the truncated Tat protein was found to contain only a single Tat binding site on one or the other of the two stems, which was visualized most clearly by footprint analysis of the 5'DB (5' bulge deleted) TAR-2 RNA. Importantly, although the C2 and FL Tat:TAR complexes are sensitive to mutations in the loop of the stem, ethylation of loop residues does not disrupt binding of Tat to TAR, in fact, ethylated loop residues are enriched in the population of RNAs that bind to Tat, suggesting that ethylation at these sites may directly or indirectly (i.e., through changes in RNA conformation) promote the binding of Tat. Most importantly, these data indicate that Tat does not form hydrogen-bonding interactions with residues in the loop of TAR-2. Nevertheless, RNAse T1 protection studies indicate that the binding of Tat weakly protects residues in the loop of TAR-2 hairpins in solution, and therefore Tat might be capable of recognizing TAR loop sequences through base stacking interactions. Most importantly, these results confirm and extend the results from many earlier studies that the sequence requirements that direct binding of Tat to TAR RNA in vitro do not correspond well with the sequences critical for TAR to mediate transactivation by Tat in vivo or in vitro.

EXAMPLE 4

The Nuclear Tat-Associated Kinase (TAK) Binds to Both TAR-1 and TAR-2 RNA in a Loop-specific Manner Because the TAK(P-TEFb) nuclear carboxyl-terminal domain kinase complex has been shown to interact directly with the transactivation domain of Tat and has been shown to function as a transcriptional coactivator for Tat in vivo and in vitro, it was tested whether the RNA-binding properties of Tat might be altered upon its interaction with the TAK/P-TEFb complex in HeLa nuclear extracts. To determine whether TAK(P-TEFb) remains associated with Tat upon binding to TAR RNA, crude HeLa nuclear extracts were supplemented with Tat under conditions that support Tat-mediated transcription in vitro, and the extracts were incubated with TAR RNA-coupled beads that contain either the wild-type or loop mutant sequences. A 30 ml run-off transcription contained 25 mM Tris pH 8.0, 11% glycerol, 78 mM KCl, 17 mM NaCl, 5.2 mM $MgCl_2$, 4 mM DTT, 0.5 mM EDTA, 10 mM phosphocreatine, 600 mM in each of three ribonucleotides ATP, GTP, and CTP, 20 mM UTP, 4 mCi [a-$^{32}$P] UTP (800 Ci/mmol, 20 mCi/ml; Amersham), 100 ng of either the wild-type HIV1 or HIV2 CAT, 70 ng of the TAR deletion mutant HIV2 D34 CAT, the indicated amount of GST-cleaved Tat-1 or Tat-2, and 120 mg HeLa nuclear extract.

The HIV DNA templates were linearized with NcoI to give a run-off RNA transcript from HIV1 WT (630 nt), HIV2 WT (724 nt), and HIV2 D34 (584 nt). Following a 30 minute incubation at 30C, reactions were stopped with 200 ml stop buffer (1% sarkocyl, 100 mM NaCl, 100 mM Tris pH 8.0, 10 mM EDTA, and 25 mg/ml tRNA), phenol:chloroform extracted, and ethanol precipitated with ammonium acetate. RNA pellets were dissolved in formamide loading buffer (8 ml) and the RNAs were separated on a 6% denaturing polyacrylamide gel. TAK activity in the eluate and flow-through fractions from the TAR RNA resins was then analyzed by the GST-Tat selection procedure described by Herrmann and Rice (1993) Virol 197:601–608), followed by incubation with g-$^{32}$P-ATP to visualize the 42 kDa auto-phosphorylated (catalytic) subunit of TAK (previously identified as PITALRE; for review see Jones, K A (1997) Genes Dev 11:2593–2599).

Most of the 42 kDa TAK/P-TEFb subunit (PITALRE) that is present in HeLa nuclear extracts binds avidly to the TAR-1 and TAR-2 RNAs in the presence of their cognate Tat proteins. By contrast, the p42 TAK subunit (PITALRE) does not associate with beads lacking RNA, or with beads containing equivalent amounts of the TAR-1 or TAR-2 loop mutant RNAs. The Tat:TAK (P-TEFb) complex bind on TAR RNA could be dissociated with a high ionic-strength buffer, and is present in the eluate fractions from the TAR-1 and TAR-2 RNA resins, and not in the eluate fractions from TAR-1 and TAR-2 loop mutant RNA beads or beads lacking any RNA. As described previously by Herrmann and Rice (1993), the p42TAK subunit can phosphorylate recombinant GST-Tat-2 but not GST-Tat-1, and consequently the phosphorylation of the GST-Tat-2 protein is detected only in those reactions that contain the 42 kDa protein kinase.

To demonstrate that the 42 kDa kinase is associated specifically with the transactivation domain of the HIV-1 Tat protein, the regions of Tat that were necessary for interaction with the kinase are identified. A 16 ml reaction volume contained 12% glycerol, 20 mM NaCl, 70 mM KCl, 1.3 mM DTT, 30 mM Tris (pH 8.0), 0.01% NP-40, 5.5 mM $MgCl_2$, 850 ng dI-C, 500 ng rI-C, 30 mM phosphocreatine, 0.4 mM in each of the three ribonucleotides rATP, rGTP, and rCTP, 13 uM rUTP, the indicated amount of Tat, and, unless indicated otherwise, 2 ng labelled TAR. HeLa total RNA was added during complex formation to maintain specificity. The reaction was allowed to proceed for 15 minutes at 30C or on ice and the resulting complex loaded on a pre-run 4% Tris-glycine gel (5 Watts, 2.5 hours for gels at room temperature; 7 Watts, 2.5 hours for gels at 4C). 5% glycerol was added to both the running buffer and the gel.

The 42 kDa TAK subunit does not associate with two different Tat-1 transactivation domain mutants (C22G, P18IS) either in extract or following fractionation of the extract over the TAR-1 RNA resin. Similar results are obtained with the Tat-1 K41A mutant, and with mutant Tat-2 proteins that contain truncations in the transactivation domain. Addition of a truncated Tat-1 protein that contains the transactivation domain but lacks the ARM (Tat-1 aa1–48) to the HeLa extract blocks the ability of the wild-type Tat-2 protein to associate with the kinase as detected using antiserum specific for the Tat-2 protein. This inhibition is specific, because squelching does not occur with the comparable region of the C22G mutant Tat-1 protein. Thus the wild-type Tat 1–48 protein, but not the mutant Tat 1–48 protein, blocks the association of TAK with Tat-2 in solution and on TAR-2 RNA. These findings indicate that a complex containing Tat and TAK associates with TAR-1 and TAR-2 RNAs in a loop-specific manner that does not resemble the interaction observed between free Tat and TAR in vitro. Most importantly, the TAR RNA-binding properties of the Tat:TAK complex correlate precisely with the ability of TAR to function as a cis-acting element for Tat in transcription, as it has been characterized in vivo and in vitro.

EXAMPLE 5

Tat is Required for TAK(P-TEFb) to Associate with TAR RNA

The 42 kDa TAK subunit has recently been identified as the CDC2-related protein kinase, PITALRE, and this result was confirmed by western blot analysis with antisera specific for PITALRE. To assess whether Tat was required for the PITALRE kinase to associate with TAR RNA, HeLa nuclear extracts were incubated with TAR-1 RNA beads in the presence or absence of Tat, and the presence of 42 kDa kinase was assessed following immunoprecipitation with anti-PITALRE antibodies. Labelled and modified TAR RNA was bound to either GST-Tat-2 (99) WT or GST-Tat-2 (99) D1-77 and the complex was purified on a nondenaturing polyacrylamide gel using the gel shift conditions stated above with the following modifications per reaction: an increase to 25 ng TAR and either 500 ng of the WT or truncated GST-Tat-2 proteins. The gel was exposed to film and the desired bands were excised from the gel and eluted overnight in 2 ml of an RNA elution buffer (0.5 M ammonium acetate, 0.1% SDS). The mixture was extracted with phenol/chloroform, precipitated with ethanol without additional salt, and the pellet was washed with 80% ethanol. Cleavage of modified TAR RNA with aniline was as described (Conway and Wickens (1987) *EMBO J.* 6:4177–4184) and the RNA footprints were analyzed on a 12% denaturing polyacrylamide sequencing gel.

For RNase T1 digestion of TAR RNA, reactions were prepared with 5 mg tRNA, 25 ng TAR RNA, and 1 ml of a 1:60 dilution of RNase T1 (Boehringer, 100 units/ul) in the standard 16 ml RNA-binding reaction described above. Following a 30 min. incubation on ice, the RNA was extracted with phenol, precipitated with ethanol, and resuspended in formamide loading buffer. Importantly, the association of the 42 kDa PITALRE kinase with the TAR-1 RNA beads was found to require the HIV-1 Tat protein. Moreover, PITALRE did not effectively associate with TAR-1 when the HeLa extract was incubated with Tat-1 C22G transactivation mutant, nor with the truncated Tat-1 protein (Tat 1–48) which retains the transactivation domain but lacks the ARM. Thus the association of the PITALRE subunit of TAK/P-TEFb with TAR RNA requires both the transactivation domain of Tat as well as its arginine-rich RNA-recognition motif. These results demonstrate Tat is required for the TAK/P-TEFb transcription elongation factor complex to bind to TAR RNA in vitro.

EXAMPLE 6

Identification of a Nuclear 87 kDa Phosphoprotein Associated with CDK9

To characterize the protein constituents of the TAK/P-TEFb complex that interact with the transactivation domain of HIV-1 Tat, GST-Tat-1 (aa 1–48)-coupled beads were incubated with a crude HeLa nuclear extract, recovered, washed extensively, and analyzed by SDS-PAGE and silver-staining. Plasmid pGST-Tat-1 K41A (aa1–48) was prepared by subcloning the transactivation domain of the full-length HXB2 Tat-1 K41A protein into the BamHI and SmaI sites of pGEX-2 T (Pharmacia). All other GST-Tat constructs used in this study were described previously (Rhim et al. (1994) *J Acquir Immune Defic Syndr* 7:1116–1121). Preparation of HeLa nuclear transcription extracts was described previously (Sheridan et al. (1995)*Genes Dev* 9:2090–2104). Tat-mediated HIV transcription in vitro was analyzed by run-off assays. The reaction contains 25 mM Tris pH8.0, 11% glycerol, 75 mM KCl, 6 mM $MgCl_2$, 0.5 mM EDTA, 0.6 mM ATP, CTP and GTP, 40 mM UTP, 6 mCi [a-$^{32}$P] UTP, 150 ng of HIV-2/CAT DNA, 100 ng of HIV-2ΔTAR DNA (as internal control), and 120 mg of HeLa nuclear extracts (before and after depletion of cyclin T1). Plasmids wild-type (wt) pHIV-2/CAT and TAR-deleted pHIV-2ΔTAR/CAT (ΔTAR) were linearized with NcoI to generate 724- and 584-nucleotide run-off transcripts, respectively (Sheline et al. (1991) *Genes Dev* 5:2508–2520). The pHIV-1/CAT and alpha-globin promoter DNA constructs have been described previously (Sheline et al. (1991) *Genes Dev* 5:2508–2520). The adenovirus major late promoter (AdMLP) was cloned into a luciferase reporter vector and AdMLP transcripts were detected by primer extension with a primer specific for the luciferase gene.

20 ng of bacterial expressed, thrombin-cleaved GST/Tat-1(1–86) protein or equivalent volume of buffer was used. Primer extension assays were carried out in the same buffer condition as in the run-off assay except the extracts were preincubated with 500 ng of DNA in the absence or presence of 50 mM of DRB (Sigma) at 30° C. for 20 min before 0.33 mM of each NTPs was added. 100 ng of a-globin DNA was used as internal control with 100 ng HIV-1/CAT DNA, and 200 ng of AdMLP DNA was used with 100 ng of HIV-2/CAT DNA. Poly[d(I-C)] was used to compensate the total amount of DNA to 500 ng. All transcription was carried out at 30° C. for 30 min, stopped with 100 ml stop buffer (1% SDS, 20 mM EDTA, 0.1 M NaCl, 100 mg/ml yeast tRNA), extracted with a phenol:chloroform mixture, and precipitated with ethanol. Primer extension was carried out using $^{32}$P-labeled oligonucleotide primers that annealed to gene-specific primers.

An 87 kDa protein binds tightly to the wild-type HIV-1 Tat protein and does not bind to GST-Tat proteins containing amino acid substitutions or insertions in the transactivation domain (P18IS, C22G, K41A) which have been shown previously to destroy Tat activity in vivo (Rice and Carlotti (1990a) *J Virol* 64:1864–1868; Marciniak and Sharp (1991) *EMBO J* 10:4189–4196; Herrmann and Rice (1995) *J Virol* 69:1612–1620). Both p87 and the 42 kDa subunit (CDK9) of the TAK/P-TEFb complex are found to be phosphorylated when the GST-Tat-1 (aa 1–48) beads are incubated with $^{32}$P-ATP and analyzed by SDS-PAGE (8%).

As shown previously, CDK9 does not associate with activation domain mutant Tat proteins (Herrmann and Rice (1993) *Virol* 197:601–608; Herrmann and Rice (1995) *J Virol* 69:1612–1620). The GST-Tat-1 (aa 1–48) protein used in these experiments contains a functional transactivation domain, as demonstrated by its ability to block transcriptional activation by wild-type Tat-1 in vitro when incubated with nuclear transcription extracts at levels 1.5- to 5-fold higher than the wild-type Tat-1 protein, and comparable inhibition is observed with a mutant GST-Tat-2 (aa1–84) protein that contains an intact transactivation domain but lacks the ARM. The GST-Tat-1 (aa 1–48) and GST-Tat-2 (aa1–84) proteins do not influence basal transcription in the absence of Tat, nor do they affect transcription from HIV templates that lack TAR (DTAR). The ability of these Tat proteins to inhibit ("squelch") Tat transactivation in vitro is destroyed by mutations affecting key residues within the transactivation domain (Tat-1 K41A, Tat-1 C22G, Tat-1 P18IS, Tat-2 D8-47).

For inhibition by transdominant negative GST-Tat proteins, HeLa nuclear extracts (IN, 60 mg) were preincubated with excess amount of GST or mutant GST/Tat proteins before DNA templates, NTP mix and 20 ng of full-length Tat1 protein were added, and run-off transcription was carried out as described above. Fractions were eluted with Buffer C (20 mM Tris pH8.0, 20% glycerol, 0.2 mM EDTA, 2 mM DTT, 0.2 mM PMSF) containing 0.1 M, 0.3 M, 0.5 M or 1.0 M KCl. P11 fractions equivalent to 120 mg of nuclear extracts were incubated with 20 ng of full-length Tat1 at 30° C. for 20 min before combined with nuclear extracts that have been preincubated with 0.9 mg of GST/Tat-1 (aa 1–48), and in vitro transcription reactions were carried out as described above.

Inhibition of Tat transactivation by Tat-1 (aa 1–48) could not be overcome by the addition of exogenous wild-type Tat protein, but is restored by nuclear extract. Fractionation of the HeLa nuclear extract by phosphocellulose chromatography reveals that the p87 protein and TAK/P-TEFb kinase activity elute principally in the P0.5 fraction, as determined by SDS-PAGE and silver-staining for the p87 protein, and by phosphorylation of the GST-Tat-1 (aa1–48)-associated proteins. The P0.5MKCl fraction is able to restore Tat-activated transcription to reactions that are inhibited by incubation with GST-Tat-1 (aa 1–48). The P0.1MKCl fraction (FT) lacked p87 and TAK activity, and does not affect Tat transactivation, whereas the P1.0MKCl fraction, which lacks p87 and TAK activity, enhanced basal, but not Tat-activated, transcription in vitro. The p87 protein also co-fractionates with CDK9 when the P0.5MKCl fraction is subjected to chromatography on DEAE-Sepharose. These experiments indicate that p87 is a component of the TAK/P-TEFb complex that binds with high affinity and specificity to the transactivation domain of the HIV-1 Tat protein.

EXAMPLE 7

Molecular Cloning of cyclin T1 (p87)

To characterize the 87 kDa protein further, approximately 110 pmol of p87 was purified from 40 mg of crude HeLa nuclear extract using a the GST-Tat-1 (aa 1–48) affinity selection protocol. Protein affinity selection using GST-Tat-1 (aa 1–48)-coupled beads were performed by a modification of the procedure outlined by Herrmann and Rice ((1993) *Virol* 197:601–608; (1995) *J Virol* 69:1612–1620). Bacterial BL21(DE3) cultures containing various GST-Tat expression vectors were obtained from the NIH AIDS Research and Reference Reagent Program. All GST-Tat fusion proteins were expressed and purified as described (Rhim et al. (1994) *J Acquir Immune Defic Syndr* 7:1116–1121). When needed, the purified proteins were further concentrated on Centricon-30 as manufacture instructed (Amicon). HeLa nuclear extracts were precleared by sequential treatment with glutathione beads and GST protein-coupled beads, and incubated with 10 mg of GST-Tat fusion proteins on 15 ml beads at 4° C. for 1 h.

The beads were subsequently washed three times with Buffer D (150 mM KCl, 0.5% NP-40 and 0.05% SDS in Buffer C) and once with TKB buffer (50 mM Tris pH7.5, 5 mM $MnCl_2$, 5 mM DTT). 10 ml of the beads were then separated on a 8% SDS-PAGE and stained with silver. The remaining beads were analyzed for TAK activity as described (Herrmann and Rice (1993) *Virol* 197:601–608). The above small scale GST-beads pull-down assay was scaled up 80 times using GST/Tat48 protein (HIV-1 SF2 isolate) to produce about 1 mg (110 pmol) of the cyclin T1 protein, which was separated on a 6% SDS-PAGE preparative gel. Proteins were transferred to a PVDF membrane (MSI) and stained with amido black. The excised cyclin T1 protein was then trypsin digested and subjected to peptide sequencing using a Perkin Elmer ABI 470 or a Procise 494 protein sequencer.

Recombinant GST-CycK proteins were induced in BL21 (DE3) cells with 1 mM IPTG at 37° C. for 1 h. The cell pellet was resuspended in 1×PBS containing 1 mMPMSF, sonicated three times for 30 sec before Triton X-100 was added to 1%. Glutathione beads (Pharmacia) were incubated with the lysate at RT for 30 min and washed three times with 1×PBS containing 1% Triton-X100. GST-CycK proteins were eluted with 20 mM glutathione in 50 mM Tris-HCl, pH 7.5. Thrombin cleavage was performed by incubating the beads with 10 mg of thrombin (Sigma) at RT for 1 h in cleavage buffer (150 mM Tris pH 7.5, 150 mM NaCl, 2.5 mM $CaCl_2$), and the beads were washed two more times with 150 mM NaCl in 50 mM Tris-HCl, pH7.5.

Nine peptide sequences were determined (see Table 1).

TABLE 1

| NAME | SEQUENCE | AA POSITION |
| --- | --- | --- |
| P1 | (AN)VDPD(L)ELSY (SEQ ID NO: 11) | 29–37 |
| P2 | QQAANLL(S)DMGQ (SEQ ID NO: 12) | 39–50 |
| P3 | TSENLALTGVDHSLP (SEQ ID NO: 13) | 351–365 |
| P4 | QLENMEANVK (SEQ ID NO: 14) | 406–415 |
| P5 | SQYAY (SEQ ID NO: 15) | 416–420 |
| P6 | AAQNLL(C/S)HHD(C/S) (SEQ ID NO: 16) | 421–431 |
| P7 | (G)YSLSSXF(C/S) (SEQ ID NO: 17) | 558–566 |
| P8 | GPSEETGGAVFDHPA (SEQ ID NO: 18) | 575–589 |
| P9 | SGNTDKPRP (SEQ ID NO: 19) | 702–710 |

Microsequence analysis of nine tryptic peptide fragments that were resolved by HPLC established that p87 was an unknown protein. A BLAST computer homology search (Altschul et al. (1990) *J Mol Biol* 215:403–410) revealed that P5-7 matched an open reading frame of a cDNA sequence contained in the dBEST data base. A search of the gene bank database revealed an expressed sequence tag (EST 111460) clone that encoded several of the p87 peptides. A RACE PCR protocol was used to extend the cDNA clone to the 3' end. A human Jurkat (T-cell) cDNA library was then screened with radiolabeled probes derived from the EST cDNA and 3'RACE PCR products, and a 7.2 kB cDNA clone encompassing the entire (726 amino acid) open reading frame (ORF) as well as 5'- and 3'-untranslated leader sequences, was isolated and sequenced. Inspection of the amino acid sequence encoded by conceptual translation of the cDNA (SEQ ID NO:2) revealed the presence of all nine peptides that were obtained from microsequence analysis of the native p87 protein (FIG. 1A; Table 1). Database searches with the predicted protein sequence identified a region at the amino terminus that is 39% identical to the cyclin box of human cyclin C, and a longer 220 amino acid region that displayed extended homology to the cyclin fold of C-type cyclins from various organisms (FIG. 1B).

Cyclin T1 is most closely related to the essential *S. pombe* C-type cyclin, Pch1(+), which was isolated through its ability to interact with CDC2, although its physiological partner has not been established (Furnari et al. (1997) *J Biol*

Chem 272:12100–12106). CDK9 (PITALRE) is a CDC2-related protein kinase (Garriga et al. (1996) Biochem J 319:293–298; Grana et al. (1994) Proc Natl Acad Sci USA 91:3834–3838) that is closely related to the non-essential S. cerevisiae CTDK1 protein (Lee and Greenleaf (1997) J Biol Chem 272:10990–10993), which forms a complex with the C-related cyclin, CTK2, and functions in vitro as a carboxyl-terminal domain kinase (Sterner et al. (1995) Mol Cell Biol 15:5716–5724). CTDK1 has been implicated to play a role in RNAPII transcription elongation, however it is not responsible for the DRB-sensitive inhibition of RNAPII elongation that is observed in yeast extracts (Lee and Greenleaf (1997) J Biol Chem 272:10990–10993).

In vitro translation of the cDNA confirmed that the intact ORF encodes a protein of 87 kDa, indicating that the ORF of the cyclin T1 gene is complete. In addition to the N-terminal region of homology with cyclins, the predicted cyclin T1 protein also contains a putative coiled-coil motif (aa 379–412), a His-rich motif (aa 497–521) and a PEST sequence at the extreme carboxy-terminus of the protein (aa 698–726; FIG. 1A). C-terminal PEST sequences are commonly found in G1 cyclins and serve to regulate protein turn-over by the cellular ubiquitination and proteolysis pathways (Rechsteiner and Rogers (1996) Trends Biochem Sci 21:267–271). Cyclin T1 is encoded by a single gene, and its genomic location has been mapped from sequence-tagged sites (STS G25423; G28091) to a position located 295.9 cR (centiRays; 1 cR=270 kb) from the top of human chromosome 12.

The I.M.A.G.E. Consortium Clone (ID 111460) containing an 0.9 kb cDNA fragment of the gene encoding human cyclin T1 was obtained from the American Type Culture Collection. The cDNA insert was sequenced on both strands using Sequenase Version 2.0 (USB) and the derived sequence was used to design primers for 3' RACE PCR. The first round RACE PCR products were amplified from a Jurkat lZAPII cDNA library using primers 5'D (5' GGAAAAGGCTGACAAAACAGCT 3': SEQ ID NO:4) and the M13 universal primer. The reaction was started with one cycle at 98° C. for 5 min., 50° C. for 2 min., and 72° C. for 40 min., and then followed with 30 cycles at 94° C. for 1 min., 50° C. for 1 min., and 72° C. for 6 min., and finished with a 15 min. incubation at 72° C. The PCR product was diluted 1:20 and used as template for a second round of PCR using the 5'E (5' CGGAATTCGGCAGGTG-GAGATAAAGCTGC 3': SEQ ID NO:5) and T7 primers. The reaction was incubated at 97° C. for 5 min. and cycled 30 times at 94° C. for 1 min., 55° C. for 30 sec., and 72° C. for 5 min., followed by a 8 min extension at 72° C. Pfu polymerase (Stratagene) was used for all PCR reactions. The 0.8 kb 3' RACE PCR products (aa 304–726) were subcloned in the EcoRI site of pGEM-7Z(f) and sequenced as described above. The full-length cyclin T1gene was obtained by screening one million phage from a lZAPII Jurkat cDNA library (Waterman et al. (1991) Genes Dev 5:656–669) using probes from the 0.9 kb cDNA (clone 111460) and the 0.8 kb 3' RACE PCR product. Probes for screening were labeled by random priming to a specific activity of $1 \times 10^9$ dpm/mg. Positive plaques were purified by rescreening, and the clone with longest insert (7.2 kb) was sequenced on both strands by automatic DNA sequencing.

Northern blot analysis with a probe derived from the region of the cyclin box (aa 1–217) revealed that the major cyclin T1 transcript (8 kb) is widely expressed in human tissues. Northern blots were performed using 32-P labeled PCR fragments (aa1–217 and aa 304–726) and mRNA from various human tissues as described by the manufacturer (Clontech). The blots were rinsed three times at room temperature with 2×SSC, 0.05% SDS, and washed twice at 50° C. for 20 min. with 0.1×SSC and 0.1% SDS prior to autoradiography. A larger transcript (approximately 9.5 kb) was also detected in peripheral blood lymphocytes (PBLs), and relatively high levels of a shorter transcript (3.0 kb) were detected exclusively in the testis. These same transcripts were also detected with a radiolabeled probe derived from the C-terminal region of the cyclin T1 gene, and, in addition, the C-terminal probe detected an abundant 3.5 kb transcript in the ovary, which did not hybridize to a probe from the cyclin box. These results indicate that cyclin T1 mRNA is expressed widely in adult human tissues, and may be spliced differentially in PBLs as well as in cells derived from the human germ-line.

EXAMPLE 8

Cyclin T1 Interacts with CDK9 in Nuclear Extracts and is Required for RNAPII Transcription Elongation in vitro To confirm that the 87 kDa Tat-associated protein in HeLa nuclear extracts is cyclin T1, polyclonal antisera were raised to a region near the carboxy-terminus of the cyclin T1 protein (FIG. 1B). For the production of polyclonal antibodies specific to cyclin T1, a His-p86II (aa 483–701) antigen was produced as a hexahistidine fusion protein using the pET-28b(+) expression plasmid (Novagen). Following induction with 1 mM IPTG at 37° C. for 5 hr., the bacterial cell pellet was solubilized in a buffer containing 10 mM Tris-HCl, pH8.0, 0.1 M $NaH_2PO_4$, and 8M urea. The fusion protein was further purified over Ni-NTA agarose as described by the manufacturer (Qiagen). Approximately 1.5 mg of His-p86II protein was loaded onto a preparative SDS-PAGE gel and transferred to a PVDF membrane (MSI), and the antigen was used to raise polyclonal antibodies in New Zealand white rabbits (Pocono Rabbit Farm & Laboratory, Inc.). Polyclonal antisera specific to cyclin T1 or CDK9 were used for immunoblots using the ECL detection method (Amersham).

Immunoprecipitates from Hela nuclear extracts incubated with the anti-cyclin T1 serum specific to cyclin T1, CDK9, or with preimmune serum were analyzed by SDS-PAGE and silver-staining or phosphorylation, and found to contain two major proteins, corresponding to the native 87 kDa cyclin T1 protein and CDK9. Proteins were visualized by staining with silver or by incubation of the beads with 32P-ATP to analyze the phosphorylated proteins. Both cyclin T1 and CDK9 which were also detected upon immunoprecipitation with anti-CDK9 (PITALRE) antisera. For immunoprecipitation reactions, aliquots of 50 ml (750 mg) of HeLa nuclear extract were diluted 1:4 with IP buffer (20 mM Tris-HCl, pH 7.9, 0.5% NP-40, 1% Triton X-100, 5 mM DTT) containing 150 mM KCl and the reactions were incubated with either 1 mg of anti-CDK9 IgG (PITALRE-CT, Santa Cruz Biotechnology), or with 1 ml of preimmune or anti-cyclin T1 antisera, at 4° C. for 4 hr. The reactions were mixed with 10 ml of Protein A Sepharose, incubated at 4° C. for 1 hr., and washed five times with 1 ml aliquots of IP buffer containing 1 M KCl. Transcription extracts were depleted of cyclin T1 using affinity-purified antiserum, which was prepared by incubating the polyclonal anti-cyclin T1 antiserum with a His-p86II affinity column coupled to Affi-Gel 10 (Bio-Rad). Antibodies were eluted with 0.1 M Glycine, pH 3.0 and neutralized immediately.

The identity of the 87 kDa and 42 kDa proteins as cyclin T1 and CDK9 was confirmed by western blot analysis of the immunoprecipitated reactions. Neither cyclin T1 nor CDK9 were detected in parallel immunoprecipitation reactions that were carried out using control (preimmune) serum. Western blot analysis also confirmed the presence of native cyclin T1 and CDK9 in TAK/P-TEFb fractions derived by GST-Tat affinity selection from HeLa nuclear extracts. As determined previously for the p87 protein detected by silver-staining, the cyclin T1 protein binds only to Tat-1 or Tat-2 proteins that carry a functional transactivation domain in a manner identical to that described previously for CDK9. These results demonstrate that the cyclin T1 cDNA encodes the 87 kDa protein identified originally as a protein that is present with CDK9 in a complex that is recognized by the transactivation domain of Tat.

Previous studies have shown that P-TEFb is critical for DRB-sensitive RNAPII transcription elongation at many promoters (Marshall et al. (1996) *J Biol Chem* 271:27176–27183; Marshall and Price (1995) *Chem* 270:12335–12338; Zhu et al. (1997) *Genes Dev* 11:2622–2632), and immunodepletion of CDK9 from HeLa nuclear extracts has been shown to inhibit RNAPII elongation as well as Tat transactivation (Mancebo et al. (1997) *Genes Dev* 11:2633–2644; Zhu et al. (1997) *Genes Dev* 11:2622–2632). To test the role of the cyclin T1-CDK9 complex in transcription, HeLa nuclear extracts were depleted of endogenous cyclin T1 by repeated incubation with anti-cyclin T1 beads. Immunodepletion was performed by incubating Protein A Sepharose (Pharmacia)-precleared HeLa nuclear extracts with affinity purified anti-cyclin T1 IgGs on Protein A beads. Control depletion reactions used either GST-specific polyclonal antiserum (Santa Cruz Biotechnology) or preimmune antiserum. Western blot analysis indicated that this procedure resulted in the loss of most (approximately 80%) of the endogenous HeLa cyclin T1 protein as well as CDK9.

Analysis of the transcriptional activity of the cyclin T1-depleted extracts revealed that the loss of cyclin T1 has only a modest effect on transcription initiation from the HIV-1 promoter and no effect on initiation of other promoters (HIV-2, a-globin and AdMLP), as assessed by primer extension with gene-specific primers that anneal within 100 nt of the RNA start site for each promoter. As expected, the short transcripts that were detected with these primers were not sensitive to inhibition by DRB. The small (two-fold) reduction in initiation at the HIV-1 promoter observed in the depleted extracts suggests that cyclin T1 might play a minor role in RNA initiation at the HIV-1 promoter. In striking contrast, however, the loss of cyclin T1 caused a dramatic reduction in the formation of long, DRB-sensitive, transcripts from both wild-type and TAR-deleted HIV promoter templates, as well as from the a-globin promoter, and TAR-dependent Tat transactivation was abolished as well. Importantly, transcription elongation was unaffected in extracts treated with control (GST) antiserum. These results indicate that cyclin T1 is required, directly or indirectly, for CDK9-stimulated elongation of transcription by RNAPII.

Wild-type Tat protein can promote the binding of nuclear TAK/P-TEFb complexes to TAR RNA, and that mutations in the activation domain of Tat or in the loop of TAR RNA are sufficient to block the interaction of TAK/P-TEFb with TAR RNA in vitro. To determine whether cyclin T1 also binds to TAR RNA-coupled beads under similar circumstances, HeLa nuclear extracts were mixed with Tat-1 and incubated with wild-type or loop mutant TAR RNA-coupled beads. The eluates from wild-type and loop mutant TAR-1 RNA beads were then analyzed by western blot for cyclin T1, CDK9 and Tat-1 protein. 750 ng of GST-Tat-1 (aa 1–86) was incubated with 500 mg of HeLa nuclear extract and bound to 10 mg of strepavidin-coupled TAR-1 RNA beads. Cyclin T1 was found to interact with wild-type, and not loop mutant, TAR-1 RNA under these conditions. Comparable levels of CDK9 and Tat-1 proteins were also found associated with wild-type TAR-1 RNA in this experiment. By contrast, only trace quantities of the unrelated CDK7 protein binds to the TAR RNA beads, and CDK7 did not discriminate between wild-type and loop mutant TAR RNAs. Native cyclin T1 protein is tightly associated with CDK9, Tat and TAR RNA in nuclear extracts.

EXAMPLE 9

Recombinant cyclin T1 Interacts Directly with the Transcriptional Activation Domain of Tat Because p87 was prominent among the nuclear proteins that could be shown to interact specifically with the Tat transactivation domain in HeLa nuclear extract, it was important to determine whether p87 could interact directly with Tat. Therefore, whether the HIV-1 and HIV-2 Tat proteins could bind to recombinant cyclin T1 protein in vitro was tested. Recombinant cyclin T1 protein was expressed in bacteria as a GST-cyclin T1 fusion protein, and the glutathione S-transferase domain was removed with thrombin cleavage. To generate a bacterial expression vector for the production of recombinant cyclin T1 (pGST-cyc K), the full-length human cyclin T1 cDNA was subcloned into the NcoI and HindIII site of pGEX-KG (Guan and Dixon (1991) *Anal Biochem* 192:262–267).

Cyclin T1 was expressed in bacteria as a GST fusion protein, and the GST domain was cleaved with thrombin prior to incubation with different HIV-1 and HIV-2 GST-Tat-coupled beads. Reactions containing 4 mg of the wild-type or mutant GST-Tat proteins were incubated with 1 mg of thrombin-cleaved recombinant cyclin T1 protein in 500 ml binding buffer (20 mM HEPES, pH 7.9, 200 mM KCl, 0.5% NP-40, 1% Triton X-100, 0.7% beta-mercaptoethanol, 0.1% BSA) at 4° C. for 4 hr. The reactions were then incubated for 30 min. with 10 ml of glutathione beads which had been preincubated with 0.1% BSA. The beads were washed three times with washing buffer (20 mM HEPES, pH 7.9, 1 M KCl, 0.5% NP-40, 1% Triton X-100, 0.7% beta-mercaptoethanol), recovered, and eluted in SDS-laemmli sample buffer. The recombinant cyclin T1 protein was incubated with wild-type and mutant GST-Tat proteins that were bound to glutathione beads. The eluates from the wild-type or mutant Tat affinity beads were analyzed by immunoblot for cyclin T1 protein using the cyclin T1-specific polyclonal antisera. The recombinant cyclin T1 protein binds to wild-type GST-Tat-1 and GST-Tat-2 proteins, as well as to truncated Tat proteins that lack the ARM but contain an intact transactivation domain. Cyclin T1 did not bind to GST-coupled beads, and binding was significantly reduced by a point mutation in the Tat-1 transactivation domain (K41A) or a deletion in Tat-2 transactivation domain (Tat-2 D8-47). Thus cyclin T1 binds in a specific manner to the transactivation domains of the HIV-1 and HIV-2 Tat proteins in vitro.

EXAMPLE 10

The Interaction of cyclin T1 with Tat Dramatically Enhances its Affinity for TAR RNA and Alters the Specificity of the Tat:TAR Interaction It has been shown previously that the binding of Tat to TAR RNA in vitro does not correlate well with the sequence requirements for TAR in Tat transactivation (for review, see Cullen, B. (1993) *Cell* 73:417–420; Jones and Peterlin (1994) *Annu Rev Biochem* 63:717–743). Most importantly, the binding of the ARM of Tat to TAR RNA does not require sequences in the loop of the RNA that are critical for Tat transactivation. Exogenous TAR RNAs were prepared from plasmids pH96 WT and pH96 30/33, which contain a single copy of the wild-type and loop mutant HIV-1 TAR RNA (+1 to +80), respectively (Sheline et al. (1991) *Genes Dev* 5:2508–2520). Plasmids pTAR2 WT and pTAR2 LM, which contain a single copy of the wild-type or double loop mutant of TAR-2 RNA (+1 to +123), respectively, and were subcloned into the HindIII and BamHI sites of pSP64 polyA vector (Promega). The identity of every plasmid cloned by PCR was confirmed by DNA sequencing using Sequenase Version 2.0 (USB).

Binding of the full-length Tat-1 protein, but not the Tat-1 ARM, is modestly affected by mutations in the loop of TAR-1 RNA in vitro, indicating that sequences in the activation domain of Tat enhance the specificity of binding, and that Tat contains an intrinsic ability to interact weakly with residues in the loop of the RNA. Tat binds with much higher affinity to TAR-2 RNA than TAR-1 RNA in vitro, and that mutations in the loop of the TAR-2 dramatically reduce binding of Tat in vitro. Indeed, free Tat binds with higher affinity to the TAR-2 loop mutant RNA than to the wild-type TAR-1 RNA in vitro. Therefore, the interaction of Tat with a cellular RNA-binding cofactor is predicted to selectively enhance the affinity of Tat for wild-type TAR-1 RNA, as well as block the residual binding of the Tat proteins to the bulge region on TAR-1 and TAR-2 loop mutant RNAs.

To determine whether the interaction of Tat with cyclin T1 alters its TAR RNA recognition properties, gel mobility shift experiments were carried out with recombinant Tat and cyclin T1 proteins and wild-type and is loop mutant HIV-1 and HIV-2 TAR RNAs. Binding of wild-type and mutant HIV-1 Tat (aa 1–86) proteins to TAR RNA in the presence or absence of recombinant cyclin T1 was analyzed by gel mobility shift experiments. Reactions contained 400 ng of GST-Tat-1 (aa 1–86), GST-Tat-1 C22G (1–86) or GST-Tat-1 P18IS(1–86) proteins either alone or together with 750 ng of GST-cyclin T1 in the presence of 5 ng of wild-type TAR-1 RNA (wt) or loop mutant TAR-1 RNA (lm). The full-length HIV-1 Tat binds weakly to wild-type TAR-1 RNA (wt), and a four base substitution of residues in the loop of TAR-1 (lm) reduced the binding of Tat by approximately three-fold. Interestingly, the binding of HIV-1 Tat to TAR-1 RNA was dramatically enhanced in the presence of cyclin T1, and this complex did not form on the loop mutant TAR-1 RNA (cycK+Tat-1). Cyclin T1 did not enhance the binding of the C22G transactivation domain mutant Tat-1 protein to TAR RNA, and interacted only very weakly with the P18IS mutant Tat-1 protein. Thus, the specific interaction of Tat with cyclin T1 dramatically enhances its affinity for TAR RNA, and efficient formation of the ternary cyclin T1-Tat:TAR complex requires the integrity of the Tat transactivation domain as well as sequences in the apical loop of the TAR RNA structure. Moreover, cyclin T1 displays no affinity for TAR RNA in the absence of Tat, indicating that the association of the cyclin with the TAR element depends entirely upon its ability to bind co-operatively with Tat to the RNA.

By contrast with TAR-1 RNA, the HIV Tat proteins bind with intrinsically higher affinity to TAR-2 RNA, and the binding of full-length Tat to TAR-2 RNA is reduced dramatically upon substitution of the conserved residues in the loop of the duplicated upper stem of the TAR-2 structure. The Tat proteins appear to bind to two or possibly three sites on TAR-2 RNA, and form several complexes in gel mobility shift experiments. In the presence of cyclin T1, a new complex was formed with Tat-2 on TAR-2 RNA, and the cyclin T1-Tat:TAR-2 ternary complex did not bind to loop mutant TAR-2 RNA.

Binding of GST-Tat-2 to TAR-2 RNA, alone and in the presence of GST-cyclin T1 were analyzed. Binding reactions contained 400 ng wild-type GST-Tat-2 (aa 1–99), or activation domain mutant GST-Tat-2Δ8–47 protein and 5ng of wild-type (wt) or loop mutant (lm) TAR-2 RNA. As observed above with TAR-1 RNA, cyclin T1 had no intrinsic affinity for RNA in the absence of Tat, and did not affect the binding of a mutant Tat-2 protein that contains the ARM but lacks the transactivation domain (Tat-2 D8-47). The binding of cyclin T1 to TAR-2 RNA is completely dependent upon its ability to interact with Tat-2 through its transcriptional activation domain. Because Tat has a higher intrinsic affinity for TAR-2 RNA than for TAR-1 RNA, the extent of co-operativity observed upon addition of cyclin T1 was less dramatic than that observed for Tat-1 on TAR-1 RNA, however, the binding of cyclin T1 and Tat-2 is highly co-operative at limiting concentrations of Tat-2, and the enhanced binding of Tat-2 to TAR-2 RNA is evident in RNase footprint protection experiments, which are more sensitive to the formation of stable complexes (see below). Cyclin T1 strongly enhances the binding of both Tat-1 and Tat-2 proteins to RNA in infected cells.

TAR-1 RNAs were synthesized using T7 RNA polymerase from Hind III-digested pH96 WT and pH96 30/33 DNAs, and TAR-2 RNAs were transcribed with SP6 RNA polymerase after linearization of pTAR2WT or pTAR2LM with HindIII. Both TAR-1 and TAR-2 loop mutants contain the same sequence alterations altered from the wild-type CUGGG sequence to CGUUU. Large scale TAR synthesis was performed in a 0.4 ml final reaction volume containing RNA synthesis buffer (40 mM Tris-HCl, pH 8.0, 2 mM spermidine, 20 mM DTT, 6 mM $MgCl_2$, 0.5 mM of each of the ribonucleoside triphosphates (rNTPs), 20 pmol linear DNA template, 0.8 units/ml T7 or Sp6 RNA polymerase (Ambion), and 100 units RNasin (USB). Reactions were incubated at 37° C. for 2 hr. For synthesis of high specific-activity TAR RNAs used for gel mobility shift experiments, 80 ml reactions contained 1 pmoL oo linear DNA template, RNA synthesis buffer, 2 mM rUTP, $^{32}$P-UTP (30 mCi, 800 Ci/mmol, 20 mCi/ml, Amersham), and 0.5 mM each of rATP, rGTP, rCTP. Reactions were incubated at 37° C. for 1 hr. and the DNA template was incubated with 2 units DNase I (Promega) per mg DNA, extracted with a phenol:chloroform mixture and precipitated with ethanol. The RNA pellet was dissolved in 0.1 M NaCl and applied to a G-50 spin column (Boehringer) prior to use, If cyclin T1 is the TAR RNA-binding cofactor for Tat, one prediction is that exogenous synthetic wild-type TAR decoy RNAs, as well as transdominant mutant Tat proteins, should compete effectively for the formation of the cyclin T1-Tat:TAR ternary complex in vitro. The binding of the cyclin T1-Tat complex to TAR-1 RNA could be effectively competed by an excess of wild-type TAR-1 or TAR-2 RNA, and was not inhibited by equivalent amounts of TAR loop mutant RNAs. Approximately 400 ng of GST-Tat-1 was incubated with 750 ng of recombinant GST-cycin T1 in the presence of 5 ng of wild-type TAR-1 RNA. Reactions contained no competitor RNA, or unlabeled TAR-1 or TAR-2 competitor RNAs at a 100-fold, 200-fold or 400-fold molar excess to the radiolabeled RNA. The specificity of the cyclin T1-Tat:TAR complex observed here correlates precisely with the ability of these TAR decoy RNAs to block Tat-activated transcription from the HIV-1 LTR in vitro.

In addition, pre-incubation of the cyclin T1 protein with an excess of the transdominant negative mutant Tat-1 (aa 1–48) protein was sufficient to block the formation of the cyclin T1-Tat:TAR ternary complex. Reactions contained recombinant cyclin T1 and Tat proteins at the following levels: 750 ng of GST-cyclin T1, 400 ng of wild-type GST-Tat-1 (aa 1–86), 400 ng GST-Tat-2 (aa 1–48), 4 mg GST-Tat-1 (aa1–48), 400 ng GST-Tat-1 K41A (aa 1–48), 4 mg GST-Tat-1 K41A (aa 1–48). By contrast, the weak binding of free Tat to TAR-1 RNA was not inhibited by GST-Tat-1 (aa 1–48), and comparable levels of the mutant GST-Tat K41A (aa 1–48) protein did not interfere with the formation of the cyclin T1-Tat:TAR. The binding of the transdominant mutant Tat-1 (aa 1–48) protein to cyclin T1 is sufficient to prevent formation of the ternary complex with TAR RNA. This experiment also demonstrates that the ARM of Tat is critical for formation of the cyclin T1-Tat:TAR complex, because the transdominant GST-Tat-1 (aa1–48) protein has no affinity for TAR RNA, either alone or in the presence of cyclin T1.

EXAMPLE 11

The cyclin T1-Tat Complex Protects Sequences in the Loop And Upper Stem of the TAR RNA in RNase Footprint Experiments To assess the interaction of the cyclin T1-Tat complex with TAR RNA in greater detail, solution RNase footprint experiments are carried out. TAR-1 and TAR-2 RNAs used for the RNase and carboxymethylation interference footprint experiments were 3' end-labeled with T4 RNA ligase and [5'-$^{32}$P] pCp as described previously (Churcher et al. (1993) *J Mol Biol* 230:90–110). A 20 ml reaction contained 50 mM Tris-HCl, pH 8.0, 3 mM DTT, 10 mM MgCl$_2$, 25 mM NaCl, 50 mM ATP, 200 pmole RNA transcribed from pTAR-2 WT, 65 mCi [$^{32}$P]pCp (3000 Ci/mmole, Andotek), 40 u T4 RNA ligase (NEB), 80 u RNasin (USB), 25 mg/ml BSA, and 10% DMSO. Following an incubation overnight at 4° C., the RNA was extracted, precipitated and passed through a G-50 spin column. The typical yield was 2.5×10$^4$ cpm/pmole RNA. End-labeled TAR probes were purified on a 6% denaturing polyacrylamide gel and eluted prior to use. DEPC-treatment of TAR RNA was carried out by incubating 2 mg of 3'-end labeled TAR-2 RNA with 1 ml DEPC for 7 min. at 90° C. The RNA was chilled rapidly on ice, applied to a G-50 spin column and precipitated with ethanol prior to use.

Radiolabeled TAR-1 RNA was incubated with recombinant Tat-1, cyclin T1, or the cyclin T1-Tat-1 complex and subjected to partial digestion with different ribonucleases (RNase T1, cobra venom RNase, RNase A). 3' end-labeled TAR-1 was pre-incubated in the absence of protein or in the presence of GST-Tat-1 (aa 1–86), recombinant cyclin T1, or the cyclin T1-Tat-1 complex. Reactions were treated with single-strand-specific RNase T1, double-strand-specific RNase CV, or single-strand specific RNase A. Binding of the cyclin T1-Tat-1 complex resulted in a specific protection of sequences in the upper stem and loop of the TAR-1 RNA hairpin. No specific binding to TAR-1 RNA could be observed with cyclin T1 or Tat-1 alone. Thus, under the stringent binding conditions used in this experiment, only the cyclin T1-Tat complex binds with sufficient affinity to protect TAR-1 RNA from nuclease digestion. Under these conditions, the binding of Tat-1 and cyclin T1 to TAR-1 RNA is highly co-operative and results in the formation of a stable complex in which the upper stem and loop sequences are protected specifically. In RNase footprint experiments carried out with TAR-2 RNA, the binding of the Tat-2 protein to TAR-2 RNA resulted in the formation of a nuclease hypersensitive site at G57 and weak protection of sequences in the bulge of and loop of the 5' hairpin stem.

Using gel mobility shift experiments, it is shown that recombinant cyclin T1 did not interact with TAR-1 or TAR-2 RNA in the absence of Tat. However, the cyclin T1-Tat-2 complex demonstrated strong protection over sequence in the loop and stem of both of the duplicated TAR-2 hairpin structures. Gel mobility shift reactions (16 ml final reaction volume) contained 30 mM Tris-HCl, pH 8.0, 12% glycerol, 70 mM KCl, 1.3 mM DTT, 0.01% NP-40, 5.5 mM MgCl$_2$, 5 ng of labeled TAR-1 or TAR-2 RNA and wild-type or mutant Tat proteins. Reactions were incubated for 30 min. at 4° C. and the RNA-binding complexes were separated on a pre-run 4% Tris-Glycine gel (7 watts, 2.5 h at 40° C). Reactions for RNase footprint experiments contained 1 mg tRNA, 400 ng GST-Tat-1 (aa1–86) or GST-Tat-2 (aa1–99), 750 ng GST-cycK, and 2.5 ng each of the 3' end-labeled TAR-1 or TAR-2 RNA probes. RNA-binding complexes were formed for 30 min. at 4° C. and subsequently treated with 1 ml each of either RNase T1 (0.3 unit, Boehringer), RNase CV (0.035 u, Pharmacia), or RNase A (0.6 ng, Boehringer) on ice for 15 min. Following the addition of 85 ml of stop buffer (100 mM Tris-HCl, pH 8.0, 1% Sarkosyl, 100 nM NaCl, 10 mM EDTA, and 25 mg/ml tRNA), the RNA was isolated and analyzed on a 12% denaturing polyacrylamide gel. Binding of the cyclin T1-Tat-2 complex was highly specific and did not result in protection of RNA sequences outside or between the two TAR-2 RNA stem-loop structures. Cyclin T1 strongly enhances the specific interaction of Tat-2 with TAR-2 RNA in vitro.

Carboxymethylation-interference experiments show that DEPC-treatment of residues in the loop of TAR-2 RNA does not interfere with the ability of free Tat-2 to bind to TAR-2 RNA, which raises the possibility that Tat may not recognize residues in the loop of TAR RNA by direct hydrogen-bonding interactions. For the carboxymethylation interference footprints, 25 ng of end-labeled, DEPC-modified TAR-2 RNA was incubated with GST-Tat-2 (aa 1–99) in the presence or absence of recombinant cyclin T1 (GST-cycK) and the complex was purified on a nondenaturing polyacrylamide gel. The modified TAR RNA was isolated from the complex, cleaved with aniline, and analyzed on a 12% denaturing polyacrylamide sequencing gel. RNase T1 digestion of TAR-2 RNA was carried out in standard 16 ml gel shift reactions with 5 mg tRNA, 25 ng TAR RNA, and 1 ml of a 1:60 dilution of RNase T1 (Boehringer, 100 units/ml), and the reaction was incubated for 30 min. on ice.

To determine whether the association of cyclin T1 with Tat-2 alters the mechanism of loop-specific binding to TAR-2 RNA, complexes formed between DEPC-treated TAR-2 RNA and Tat-2 or the cyclin T1-Tat-2 complex were isolated from native gels, and the RNA was excised and cleaved with analine. A number of specific contacts were observed between Tat or cyclin T1-Tat-2 and the bulge regions of the two TAR-2 upper stem-loop structures. However, DEPC modification of base nitrogens in the loop of the two TAR-2 hairpins did not inhibit binding of either Tat-2 or the cyclin T1-Tat-2 complex. Thus the interaction between cyclin T1 and Tat-2 does not change the pattern of direct contacts with TAR-2 RNA that can be detected by DEPC-interference interference footprint experiments, but enhances the affinity of Tat-2 for TAR RNA and protects sequences in the loop of TAR-2 RNA from nuclease digestion.

FIG. 2 shows a biochemical view of the interaction of Tat with the cyclin T1, and the subsequent co-operative binding of Tat and the TAK/P-TEFb complex to TAR RNA. In this view, Tat interacts through specific residues in the transactivation domain with the cyclin T1 subunit of a pre-existing nuclear TAK/P-TEFb complex that also contains CDK9. The interaction of Tat with cyclin T1 alters its conformation in a manner that greatly enhances the affinity and specificity of the Tat:TAR interaction. Co-operative binding of the cyclin T1-Tat complex to TAR RNA would serve to stabilize the association of CDK9, and any other components that may reside in the cyclin T1-CDK9 complex, with nascent TAR RNA at the HIV-1 promoter. The functional target(s) for CDK9 phosphorylation at the HIV-1 promoter may be the carboxyl-terminal domain or specific elongation factors that function in a carboxyl-terminal domain-dependent manner.

While the invention has been described in detail with reference to certain preferred embodiments thereof, it will be understood that modifications and variations are within the spirit and scope of that which is described and claimed.

That which is claimed is:

1. Isolated nucleic acid encoding a Tat-associating polypeptide, or functional fragments thereof, wherein said polypeptide has a molecular weight of about 87 kDa and participates as a constituent of the TAK/TEFb complex, and wherein said polypeptide modulates Tat transactivation by enhancing the affinity of the Tat protein for TAR RNA.

2. A nucleic acid according to claim 1, wherein said nucleic acid, or functional fragments thereof, is selected from:
   (a) nucleic acid encoding the amino acid sequence set forth in SEQ ID NO:2, or
   (b) nucleic acid that hybridizes to the DNA of (a) under low stringency conditions, wherein said DNA encodes biologically active cyclin T1, or
   (c) nucleic acid degenerate with respect to (b) above, wherein said DNA encodes biologically active cyclin.

3. A nucleic acid according to claim 1, wherein the nucleotide sequence of said nucleic acid is as set forth in SEQ ID NO:1.

4. A vector containing nucleic acid according to claim 1.

5. Recombinant cells containing the nucleic acid of claim 1.

6. Single strand DNA primers for amplification of cyclin T1 nucleic acid, wherein said primers comprise a nucleic acid portion of the nucleic acid according to claim 1.

7. A probe comprising at least a contiguous 15 nucleotide portion of the nucleic acid according to claim 1 sufficient to hybridize to DNA encoding a Tat-associating polypeptide, wherein said probe is labeled with a readily detectable substituent.

8. A transgenic animal expressing at least one Tat-associating about 87 kDa and participates as a constituent of the TAK/TEFb complex, and wherein said polypeptide, or functional fragments thereof, wherein said polypeptide has a molecular weight of polypeptide modulates Tat transactivation by enhancing the affinity of the Tat protein for TAR RNA.

9. A method for expression of a Tat-associating polypeptide, said method comprising culturing cells of claim 5 under conditions suitable for expression of said polypeptide.

10. A complex comprising:
    a Tat-associating polypeptide, or functional fragments thereof, wherein said polypeptide has a molecular weight of about 87 kDa and participates as a constituent of the TAK/TEFb complex, and wherein said polypeptide modulates Tat transactivation by enhancing the affinity of the Tat protein for TAR RNA,
    divalent cation metal(s), and
    a Tat protein.

11. A complex according to claim 10 further comprising a protein kinase.

12. A complex comprising:
    a Tat-associating polypeptide, or functional fragments thereof, wherein said polypeptide has a molecular weight of about 87 kDa and participates as a constituent of the TAK/TEFb complex, and wherein said polypeptide modulates Tat transactivation by enhancing the affinity of the Tat protein for TAR RNA, and
    a protein kinase.

13. An antibody raised against a Tat-associating polypeptide, or functional fragments thereof, wherein said polypeptide has a molecular weight of about 87 kDa and participates as a constituent of the TAK/TEFb complex, and wherein said polypeptide modulates Tat transactivation by enhancing the affinity of the Tat protein for TAR RNA.

14. A method to dissociate the complex of claim 10, said method comprising contacting said complex with compound(s) that can reduce individual cysteine residues.

15. A method to dissociate the complex of claim 10, said method comprising contacting said complex with compound(s) that extract said divalent cation metal(s) therefrom.

16. A method to dissociate the complex of claim 15, wherein said compound is a chelating agent.

17. A method to dissociate the complex of claim 12, said method comprising contacting said complex with a cyclin-dependent kinase inhibitor.

18. A method to identify compounds which disrupt the association of divalent cation metal(s) with cyclin T1 and/or Tat protein, said method comprising:
    (a) contacting a complex with a test compound, said complex comprising divalent cation metal(s) with cyclin T1 and/or Tat protein, (b) monitoring for the presence of divalent cation metal(s) independent of cyclin T1 and/or Tat protein, and (c) identifying those compounds which induce release of divalent cation metal(s) as compounds which disrupt the association of divalent cation metal(s) complex with cyclin T1 and/or Tat protein.

19. A method according to claim 18, wherein said test compound is a chelator.

20. A method to identify compounds which disrupt complex comprising Tat protein, divalent cation metal(s) and cyclin T1; said method comprising:

(a) contacting a host cell with a test compound, wherein said host cell comprises:
 a first fusion protein comprising a GAL4 DNA binding domain, operatively associated with the cyclin T1 binding region of Tat protein,
 a second fusion protein comprising an activation domain, operatively associated with the Tat binding region of cyclin T1,
 divalent cation metal(s), and
 a reporter construct comprising a GAL4 response element operatively linked to a reporter gene; and (b) selecting those test compounds which cause reduced expression of the reporter gene product as compounds which disrupt complex comprising Tat protein, divalent cation metal(s) and cyclin T1.

21. A method for the modulation of Tat transactivation in a biological system, said method comprising contacting said system with an effective amount of a compound identified according to the method of claim 20, thereby modulating said Tat transactivation.

22. A method to identify compounds which disrupt complex comprising Tat protein, divalent cation metal(s) and cyclin T1; said method comprising:

(a) contacting a host cell with a test compound, wherein said host cell comprises:
 a first fusion protein comprising an activation domain, operatively associated with the cyclin T1 binding region of Tat protein,
 a second fusion protein comprising a GAL4 DNA binding domain, operatively associated with the Tat binding region of cyclin T1,
 divalent cation metal(s), and
 a reporter construct comprising a GAL4 response element operatively linked to a reporter gene; and (b) selecting those test compounds which cause reduced expression of the reporter gene product as compounds which disrupt complex comprising Tat protein, divalent cation metal(s) and, cyclin T1.

23. A method for the modulation of Tat transactivation in a biological system, said method comprising contacting said system with an effective amount of a compound identified according to the method of claim 22, thereby modulating said Tat transactivation.

24. A method to identify compounds which disrupt complex comprising CDK9 and cyclin T1, said method comprising:

(a) contacting a host cell with a test compound, wherein said host cell comprises:
 a first fusion protein comprising a GAL4 DNA binding domain, operatively associated with CDK9,
 a second fusion protein comprising an activation domain, operatively associated with cyclin T1, and
 a reporter construct comprising a GAL4 response element operatively linked to a reporter gene; and (b) selecting those test compounds which cause reduced expression of the reporter gene product as compounds which disrupt complex comprising CDK9 and cyclin T1.

25. A method for the modulation of Tat transactivation in a biological system, said method comprising contacting said system with an effective amount of a compound identified according to the method of claim 24, thereby modulating said Tat transactivation.

26. A method to identify compounds which disrupt complex comprising CDK9 and cyclin T1, said method comprising:

(a) contacting a host cell with a test compound, wherein said host cell comprises:
 a first fusion protein comprising an activation domain, operatively associated with CDK9,
 a second fusion protein comprising a GAL4 DNA binding domain, operatively associated with cyclin T1, and
 a reporter construct comprising a GAL4 response element operatively linked to a reporter gene; and (b) selecting those test compounds which cause reduced expression of the reporter gene product as compounds which disrupt complex comprising CDK9 and cyclin T1.

27. A method for the modulation of Tat transactivation in a biological system, said method comprising contacting said system with an effective amount of a compound identified according to the method of claim 26, thereby modulating said Tat transactivation.

28. A method to identify compounds which block the interaction of the cyclin T1:Tat complex with TAR RNA, said method comprising:

(a) contacting a host cell with a test compound, and (b) selecting those test compounds which cause reduced expression of the reporter nucleic acid product as compounds which block the interaction of the cyclin T1:Tat complex with TAR RNA;

wherein said host cell comprises a Tat protein, divalent cation metal, cyclin T1, CDK9 and a reporter construct comprising a TAR RNA operatively linked to nucleic acid encoding a reporter protein.

29. A method for the modulation of Tat transactivation in a biological system, said method comprising contacting said system with an effective amount of a compound identified according to the method of claim 28, thereby modulating said Tat transactivation.

30. A method to identify compounds which disrupt complex comprising Tat protein, divalent cation metal(s) and cyclin T1, said method comprising:

(a) contacting an affinity matrix with a test compound, wherein said affinity matrix comprises:
 an affinity support,
 a Tat protein,
 divalent cation metal(s), and
 cyclin T1; and (b) selecting those test compounds which cause the release of Tat protein, divalent cation metal(s) and/or cyclin T1 from said support as compounds which disrupt complex comprising Tat protein, divalent cation metal(s) and cyclin T1.

31. A method for the modulation of Tat transactivation in a biological system, said method comprising contacting said system with an effective amount of a compound identified according to the method of claim 30, thereby modulating said Tat transactivation.

32. A method according to claim 30, wherein said Tat protein, divalent cation metal(s) and/or cyclin T1 is operatively associated with a label.

33. A method to identify compounds which disrupt the interaction of the cyclin T1:Tat complex with TAR RNA, said method comprising:

(a) contacting an affinity matrix with a test compound, (b) selecting those test compounds which cause the release of TAR RNA from said support as compounds which disrupt the interaction of the cyclin T1:Tat complex with TAR RNA;

wherein said affinity matrix comprises an affinity support, a cyclin T1, divalent cation metal(s), a Tat protein, and a TAR RNA.

34. A method for the modulation of Tat transactivation in a biological system, said method comprising contacting said system with an effective amount of a compound identified according to the method of claim 33, thereby modulating said Tat transactivation.

35. A method to treat a subject infected with HIV, said method comprising administering to said subject an effective amount of an antibody according to claim 13.

36. A nucleic acid according to claim 1, wherein said polypeptide comprises a cyclin groove and associates with Tat protein.

37. A nucleic acid according to claim 36, wherein said polypeptide comprises:

an N-terminal cyclin box, a coiled-coil domain, histidine-rich domain and

C-terminal PEST domain.

38. A nucleic acid according to claim 1, wherein said nucleic acid hybridizes, under low stringency conditions, to nucleotides 1–1440 set forth in SEQ ID NO:1.

39. A nucleic acid according to claim 1, wherein said nucleic acid encodes a polypeptide comprising the amino acid residues 1–380 as set forth in SEQ ID NO:2.

40. A nucleic acid according to claim 39, wherein said nucleic acid encodes a polypeptide comprising substantially the same amino acid sequence as set forth in SEQ ID NO:2.

41. An isolated nucleic acid encoding a Tat-associating polypeptide(s), or functional fragments thereof, wherein said nucleic acid hybridizes, under low stringency conditions, with a nucleotide sequence as set forth in nucleic acids 1–1440 of SEQ ID NO:1, and wherein said polypeptide modulates Tat transactivation by enhancing the affinity of the Tat protein for TAR RNA.

42. An isolated nucleic acid encoding a Tat-associating polypeptide, or functional fragments thereof, wherein said polypeptide comprises an N-terminal cyclin box and a coiled-coil domain, and wherein said polypeptide is present in a complex that is recognized by the transactivation domain of a Tat protein.

43. An isolated nucleic acid encoding a Tat-associating polypeptide, or functional fragments thereof, wherein said polypeptide comprises an amino acid sequence containing a cyclin groove, an N-terminal cyclin box, and a coiled-coil domain, and wherein said polypeptide participates as a constituent of the TAK/TEFb complex and modulates Tat transactivation by enhancing the affinity of the Tat protein for TAR RNA.

44. An isolated nucleic acid encoding a human Tat-associating polypeptide, or functional fragments thereof, said polypeptide comprising:

an N-terminal cyclin box, a coiled-coil domain, histidine-rich domain and

C-terminal PEST domain, wherein said polypeptide participates as a constituent of the TAK/TEFb complex, and modulates Tat transactivation by enhancing the affinity of the Tat protein for TAR RNA.

45. An isolated nucleic acid encoding a Tat-associating polypeptide containing an immunogenic epitope, wherein said polypeptide is encoded by nucleic acid that comprises a nucleotide sequence that hybridizes, under low stringency conditions, to nucleotides 1446–2103 as set forth in SEQ ID NO:1, wherein said polypeptide participates as a constituent of the TAK/TEFb complex, and wherein said polypeptide modulates Tat transactivation by enhancing the affinity of the Tat protein for TAR RNA.

46. Nucleic acid encoding an epitope of a Tat-associating polypeptide, wherein said nucleic acid hybridizes, under low stringency conditions, to nucleotides 1446–2103 as set forth in SEQ ID NO:1.

* * * * *

UNITED STATES PATENT AND TRADEMARK OFFICE
CERTIFICATE OF CORRECTION

PATENT NO. : 6,284,456 B1
DATED : September 4, 2001
INVENTOR(S) : Jones et al.

It is certified that error appears in the above-identified patent and that said Letters Patent is hereby corrected as shown below:

<u>Column 1,</u>
After the title, insert the following paragraph and heading therefor:

-- <u>ACKNOWLEDGEMENT</u>

This invention was made with United States Government support under Grant No. AI-33924, awarded by the National Institutes of Health. The Government has certain rights in this invention. --

Signed and Sealed this

Thirtieth Day of April, 2002

*Attest:*

JAMES E. ROGAN
*Director of the United States Patent and Trademark Office*

*Attesting Officer*